United States Patent
Kwak et al.

(10) Patent No.: US 10,894,768 B2
(45) Date of Patent: Jan. 19, 2021

(54) SALT OF (R)-($_1$-METHYLPYRROLIDINE-$_3$-YL)METHYL($_3'$-CHLORO-$_{4'}$-FLUORO-[$_{1,1'}$-BIPHENYL]-$_2$-YL) CARBAMATE AND CRYSTAL FORM THEREOF

(71) Applicant: Dong-A St Co., Ltd., Seoul (KR)

(72) Inventors: Woo Young Kwak, Seoul (KR); Chang-Yong Shin, Seoul (KR); Punna Reddy Ullapu, Seoul (KR); Sun-Ho Choi, Seoul (KR); Min-Jung Lee, Seoul (KR); Ji-Su Kim, Seoul (KR)

(73) Assignee: Dong-A St Co., Ltd., Seoul (KR)

( * ) Notice: Subject to any disclaimer, the term of this patent is extended or adjusted under 35 U.S.C. 154(b) by 0 days.

(21) Appl. No.: 16/328,492

(22) PCT Filed: Aug. 26, 2016

(86) PCT No.: PCT/KR2016/009558
§ 371 (c)(1),
(2) Date: Feb. 26, 2019

(87) PCT Pub. No.: WO2018/038297
PCT Pub. Date: Mar. 1, 2018

(65) Prior Publication Data
US 2019/0194129 A1   Jun. 27, 2019

(51) Int. Cl.
*C07D 207/09* (2006.01)
*A61K 31/40* (2006.01)
*C07D 207/08* (2006.01)

(52) U.S. Cl.
CPC ............ *C07D 207/09* (2013.01); *A61K 31/40* (2013.01); *C07D 207/08* (2013.01); *C07B 2200/13* (2013.01)

(58) Field of Classification Search
CPC .................................................. C07D 207/09
See application file for complete search history.

(56) References Cited

U.S. PATENT DOCUMENTS

| 9,828,339 | B2 * | 11/2017 | Kim | ........................ A61P 25/18 |
| 2010/0105658 | A1 | 4/2010 | Nagashima et al. | |
| 2014/0080800 | A1 | 3/2014 | Holson et al. | |
| 2016/0176816 | A1 * | 6/2016 | Kim | .................... C07D 207/08 514/428 |

FOREIGN PATENT DOCUMENTS

| EP | 0747355 A1 | 12/1996 | |
| KR | 10-2006-0129017 | 12/2006 | |
| KR | 10-2015-0014673 | 2/2015 | |
| WO | WO-2015016511 A1 * | 2/2015 | ........... C07D 207/08 |

OTHER PUBLICATIONS

Thompson et al., Current Medicinal Chemistry, Oct. 2002, 9(19), pp. 1751-1762. (Year: 2002).*
Paulekuhn et al., Journal of Medicinal Chemistry, 2007, 50, pp. 6665-6672. (Year: 2007).*
ISR/KR, International Search Report for PCT/KR2016/009558 (dated May 23, 2017).
Kim, Ji-Su, Academic Thesis: Study on Polymorphism of DA8010 (Aug. 26, 2015), Duksung Women's University, Korea (Creative Commons Deed—https://creativecommons.org/licenses/by-nc-nd/2.0/kr/legalcode ).
Graul, et al., "Tolterodine—Agent for Urinary Incontinence, Muscarinic Receptor Antagonist," Drugs of the Future 1996, 22(7):733-737.
Martel, et al., "Revatropate—Bronchodilator, Muscarinic $M_3$ Antagonist," Drugs of the Future 1997, 22(2):135-137.
Graul, et al., "Darifenacin—Agent for Irritable Bowel Syndrome, Agent for Urinary Incontinence, Muscarinic $M_3$ Antagonist," Drugs of the Future 1996, 21(11):1105-1108.
Fisher (1997) Muscarinic agonists for the treatment of Alzheimer's disease: progress and perspectives, Expert Opinion on Investigational Drugs, 6:10, 1395-1411.
Bastin et al., "Salt Selection and Optimisation Procedures for Pharmaceutical New Chemical Entities", Organic Process Research & Development, 4:427-435 (2000).
Caira, Chrystalline Polymorphism of Organic Compounds, Topics in Current Chemistry, vol. 198, Feb. 26, 1999 (46 pages).
Columbian Office Action for App No. NC2019/0001740, filed May 13, 2020 (with English translation) (16 pages).
UA Office Action for App No. 2019 02823, dated Oct. 28, 2020 (with English translation) (19 pages).
Yu et al., Physical characterization of polymorphic drugs: an integrated characterization strategy, PSTT Reviews: Research Focus 1(3)118-127 (Jun. 1998).

* cited by examiner

*Primary Examiner* — Laura L Stockton
(74) *Attorney, Agent, or Firm* — Fish & Richardson P.C.

(57) ABSTRACT

The present invention relates to a novel salt of (R)-(1-methylpyrrolidine-3-yl)methyl(3'-chloro-4'-fluoro-[1,1'-biphenyl]-2-yl)carbamate and a crystal form thereof. Also, the novel salt of (R)-(1-methylpyrrolidine-3-yl)methyl(3'-chloro-4'-fluoro-[1,1'-biphenyl]-2-yl)carbamate and the crystal form thereof according to examples of the present invention have remarkably excellent stability, hygroscopicity and solubility.

32 Claims, 19 Drawing Sheets

SALT OF (R)-(1-METHYLPYRROLIDINE-3-YL)METHYL(3'-CHLORO-4'-FLUORO-[1,1'-BIPHENYL]-2-YL)CARBAMATE AND CRYSTAL FORM THEREOF

CROSS-REFERENCE TO RELATED APPLICATION

This application is a U.S. National Phase application under 35 U.S.C. § 371 of International Patent Application No. PCT/KR2016/009558, filed Aug. 26, 2016, the contents of which are hereby incorporated by reference in their entirety.

TECHNICAL FIELD

The present invention relates to a novel salt of (R)-(1-methylpyrrolidine-3-yl)methyl(3'-chloro-4'-fluoro-[1,1'-biphenyl]-2-yl)carbamate and a crystal form thereof.

BACKGROUND

A muscarine receptor is variously present in the whole body ranging from a human brain to a salivary gland, wherein this receptor is a member of a G protein-coupled receptor and subdivided into five subtypes from M1 to M5. Out of these subtypes, M1, M2 and M3 receptors have been extensively clarified about their pharmacological properties in animal and human tissues. The muscarine M1 receptor is mainly expressed in a cerebral cortex and is involved in regulating higher cognitive functions. The M2 receptor is mainly present in heart and bladder smooth muscles and is involved in regulating a heartbeat. The M3 receptor is extensively expressed in many peripheral tissues and is known to be involved in an irritation of the gastrointestinal tract and urinary tract and salivation. M4 and M5 receptors are present in the brain, wherein the M4 receptor is mainly involved in exercise, but almost nothing has been known about a role of the M5 receptor.

In general, it is found that muscarine receptor antagonists are useful in treating various diseases, for example, a chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, hypersalivation syndrome and the like. (See Invest. Drugs, 1997, 6 (10), 1395-1411, Drugs Future, 1997, 22 (2) 135-137, Drugs Future, 1996, 21(11), 1105-1108, Drugs Future, 1997, 22 (7), 733-737).

Out of the muscarine receptor subtypes, the M2 and M3 receptors are also predominantly present in the human bladder, wherein such M2 and M3 receptors are known to play a role in regulating a bladder contraction mechanism. The M2 receptor is present in the bladder in an amount of at least three times more than the M3 receptor, but the M2 receptor plays a role in inhibiting a bladder relaxation through a beta receptor rather than being directly involved in a bladder contraction, such that the M3 receptor is considered to perform the most leading role in the bladder contraction. Thus, a selective antagonist of the M3 receptor shows an excellent inhibitory effect on a muscarinic bladder contraction, but also inhibits a salivary gland secretion at the same time, thus causing xerostomia.

The Korean Unexamined Patent Application Publication No. 2015-0014673 discloses (R)-(1-methylpyrrolidine-3-yl)methyl(3'-chloro-4'-fluoro-[1,1'-biphenyl]-2-yl)carbamate represented by a following formula A, which selectively binds to the muscarine M3 receptor to show a working activity:

[Formula A]

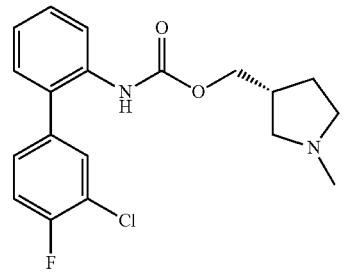

On the other hand, a compound needs to have not only preferable biological properties, but also physical properties enough to allow a use thereof in preparing a pharmaceutical composition such that the compound may be considered, as a candidate material for being developed as a drug. In particular, such compound needs to form a stable, preferably crystalline solid, which may be easily prepared and formulated into a dosage form.

However, a compound of the formula A is a foam or oil compound and has a disadvantage in that the compound is not suitable to be developed as a drug and is not easy to handle in an industrial aspect. Accordingly, the present inventors have searched for a novel salt of (R)-(1-methylpyrrolidine-3-yl)methyl(3'-chloro-4'-fluoro-[1,1'-biphenyl]-2-yl)carbamate and a crystal form thereof, which is suitable to be developed as the drug and is improved to be more easily handled in the industrial aspect. As a result, the present inventors have completed the novel salt of (R)-(1-methylpyrrolidine-3-yl)methyl(3'-chloro-4'-fluoro-[1,1'-biphenyl]-2-yl)carbamate and the crystal form thereof, which have a strong crystallinity and a non-hygroscopicity and have a remarkable decrease in a content of impurities during preparation.

PRIOR ART REFERENCE

Patent Document

Korean Unexamined Patent Application Publication No. 2015-0014673

DETAILED DESCRIPTION OF THE INVENTION

Technical Problem

An objective of the present invention is to provide a novel salt of (R)-(1-methylpyrrolidine-3-yl)methyl(3'-chloro-4'-fluoro-[1,1'-biphenyl]-2-yl)carbamate and a crystal form thereof, having a more improved physical property such as stability of products, etc., than a conventional free base of (R)-(1-methylpyrrolidine-3-yl)methyl(3'-chloro-4'-fluoro-[1,1'-biphenyl]-2-yl)carbamate.

Technical Solution

To achieve the objective above, the present inventors have studied and thus completed an (R)-(1-methylpyrrolidine-3-yl)methyl(3'-chloro-4'-fluoro-[1,1'-biphenyl]-2-yl)carbamate oxalate and a crystal form thereof, having an improved stability of products, strong crystallinity, non-hygroscopicity, and a remarkably reduced content of impurities during preparation.

Hereinafter, the present invention will be described in more detail.

In the present specification, when a certain part is said to "include" a certain component, it is not meant to exclude other components, but meant to further include other components as well, unless otherwise especially specified.

The present invention provides an (R)-(1-methylpyrrolidine-3-yl)methyl(3'-chloro-4'-fluoro-[1,1'-biphenyl]-2-yl) carbamate oxalate represented by a following formula 1:

[Formula 1]

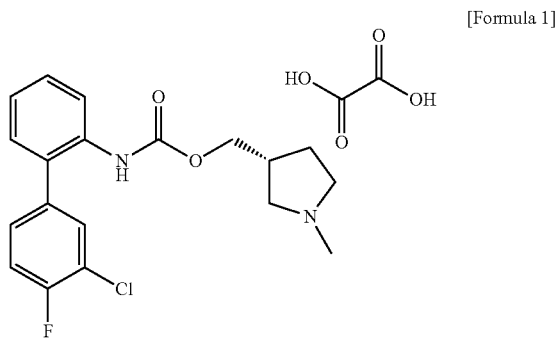

The said (R)-(1-methylpyrrolidine-3-yl)methyl(3'-chloro-4'-fluoro-[1,1'-biphenyl]-2-yl(carbamate oxalate of the present invention is a crystal. Particularly, the oxalate of the present invention may be present as forms I to VIII, and the present invention provides the said crystal forms I to VIII.

As used herein, the term "crystal form" means a crystalline solid, not containing a substantially fixed molar ratio of solvent molecules in a crystal lattice, i.e., the crystalline solid rather than a solvate.

Form I

The present invention provides a form I of (R)-(1-methylpyrrolidine-3-yl)methyl(3'-chloro-4'-fluoro-[1,1'-biphenyl]-2-yl)carbamate oxalate.

In one specific embodiment of the present invention, there is provided the said form I of (R)-(1-methylpyrrolidine-3-yl)methyl(3'-chloro-4'-fluoro-[1,1'-biphenyl]-2-yl)carbamate oxalate, in which an X-ray powder diffraction (XRPD) pattern includes at least three diffraction peaks selected from the group consisting of diffraction angles 2θ of 13.402±0.2°, 14.300±0.2°, 18.519±0.2°, 19.577±0.2° and 21.499±0.2°.

In one exemplary embodiment, there is provided the said form I of (R)-(1-methylpyrrolidine-3-yl)methyl(3'-chloro-4'-fluoro-[1,1'-biphenyl]-2-yl)carbamate oxalate, in which the XRPD pattern includes a diffraction peak at diffraction angles 2θ of 13.402±0.2°, 14.300±0.2°, 18.519±0.2°, 19.577±0.2° and 21.499±0.2°.

In other exemplary embodiment of the present invention, there is provided the form I of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 7.182±0.2°, 8.379±0.2°, 8.679±0.2°, 11.180±0.2°, 16.320±0.2°, 16.659±0.2°, 17.861±0.2°, 20.632±0.2°, 22.180±0.2°, 22.922±0.2°, 23.339±0.2°, 24.019±0.2°, 24.297±0.2°, 24.699±0.2°, 25.441±0.2°, 27.239±0.2° and 29.880±0.2°.

In another exemplary embodiment of the present invention, there is provided the said form I of (R)-(1-methylpyrrolidine-3-yl)methyl(3'-chloro-4'-fluoro-[1,1'-biphenyl]-2-yl)carbamate oxalate, in which a peak position of the XRPD pattern may be substantially the same as the peak position of FIG. 1.

In yet another exemplary embodiment of the present invention, there is provided the said form I of (R)-(1-methylpyrrolidine-3-yl)methyl(3'-chloro-4'-fluoro-[1,1'-biphenyl]-2-yl)carbamate oxalate, which has an onset temperature of 121.85° C. (±0.5° C.) and an endothermic peak of 126.96° C. (±0.5° C.) during a differential scanning calorimetry (DSC) analysis, if a heating rate is 20° C./min. More preferably, the DSC endothermic peak may be substantially the same as shown in FIG. 2.

Form II

The present invention provides a form of (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the form II of (R)-(1-methylpyrrolidine-3-yl)methyl(3'-chloro-4'-fluoro-[1,1'-biphenyl]-2-yl)carbamate oxalate, in which the XRPD pattern includes at least three diffraction peaks selected from the group consisting of diffraction angles 2θ of 13.439±0.2°, 14.481±0.2°, 18.501±0.2°, 21.779±0.2° and 23.358±0.2°.

In another exemplary embodiment, there is provided the said form II of (R)-(1-methylpyrrolidine-3-yl)methyl(3'-chloro-4'-fluoro-[1,1'-biphenyl]-2-yl)carbamate oxalate, in which the XRPD pattern includes a diffraction peak at diffraction angles 2θ of 13.439±0.2°, 14.481±0.2°, 18.501±0.2°, 21.779±0.2° and 23358±0.2°.

In one exemplary embodiment of the present invention, there is provided the said form II of (R)-(1-methylpyrrolidine-3-yl)methyl(3'-chloro-4'-fluoro-[1,1'-biphenyl]-2-yl) carbamate oxalate, in which the XRPD pattern further includes at least one diffraction peak selected from the group consisting of diffraction angles 2θ of 8.360±0.2°, 11.340±0.2°, 16.401±0.2°, 16.739±0.2°, 17.360≅0.2°, 17.938±0.2°, 22.179±0.2°, 24.299±0.2°, 24.641±0.2°, 25.500±0.2°, 26.422±0.2°, 27.260±0.2°, 28.201±0.2° and 29.878±0.2°.

In other exemplary embodiment of the present invention, there is provided the said form II of (R)-(1-methylpyrrolidine-3-yl)methyl(3'-chloro-4'-fluoro-[1,1'-biphenyl]-2-yl) carbamate oxalate, in which the peak position of the XRPD pattern may be substantially the same as the peak position of FIG. 10.

In another exemplary embodiment of the present invention, there is provided the said form H of (R)-(1-methylpyrrolidine-3-yl)methyl(3'-chloro-4'-fluoro-[1,1'-biphenyl]-2-yl)carbamate oxalate, which has the onset temperature of 127.39° C. (±0.5° C.) and the endothermic peak of 130.20° C. (±0.5° C.) during the DSC analysis, if the heating rate is 20° C./min. More preferably, the DSC endothermic peak may be substantially the same as shown in FIG. 11.

Form III

The present invention provides a form of (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the said form III of (R)-(1-methylpyrrolidine-3-yl)methyl(3'-chloro-4'-fluoro-[1,1'-biphenyl]-2-yl) carbamate oxalate, in which the XRPD pattern includes at least three diffraction peaks selected from the group consisting of diffraction angles 2θ of 10.720±0.2°, 11.018±0.2°, 14.239±0.2°, 17.880±0.2° and 21.440±0.2°.

In another exemplary embodiment, there is provided the said form III of (R) (1-methylpyrrolidine-3-yl)methyl(3'-chloro-4'-fluoro-[1,1'-biphenyl]-2-yl)carbamate oxalate, in which the XRPD pattern includes the diffraction peak at diffraction angles 2θ of 10.720±0.2°, 11.018±0.2°, 14.239±0.2°, 17.880±0.2° and 21.440±0.2°.

In one exemplary embodiment of the present invention, there is provided the said form III of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 8.700±0.2°, 13.098±0.2°, 14.959±0.2°, 15.382±0.2°, 16.701±0.2°, 17.309±0.2°, 18.680±0.2°, 19.561±0.2°, 20.560±0.2°, 22.042±0.2°, 22.762±0.2°, 23.940±0.2°, 24.141±0.2°, 26.855±0.2°, 27.379±0.2° and 29.006±0.2°.

In other exemplary embodiment of the present invention, there is provided the said form III (R)-(1-methylpyrrolidine-3-yl)methyl(3'-chloro-4'-fluoro-[1,1'-biphenyl]-2-yl)carbamate oxalate, in which the peak position of the XRPD pattern may be substantially the same as the peak position of FIG. 12.

In another exemplary embodiment of the present invention, there is provided the said form III of (R)-(1-methylpyrrolidine-3-yl)methyl(3'-chloro-4'-fluoro-[1,1'-biphenyl]-2-yl)carbamate oxalate, which has the onset temperature 123.68° C. (±0.5° C.) and the endothermic peak of 128.37° C. (±0.5° C.) during the DSC analysis, if the heating rate is 20° C./min. More preferably, the DSC endothermic peak may be substantially the same as shown in FIG. 13.

Form IV

The present invention provides a form (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the said form IV of (R)-(1-methylpyrrolidine-3-yl)methyl(3'-chloro-4'-fluoro-[1,1'-biphenyl]-2-yl)carbamate oxalate, in which the XRPD pattern includes at least three diffraction peaks selected from group consisting of diffraction angles 2θ of 16.642±0.2°, 17.839±0.2°, 20.981±0.2°, 21.580±0.2° and 22.701±0.2°.

In another exemplary embodiment, there is provided the said form IV of (R)-(1-methylpyrrolidine-3-yl)methyl(3'-chloro-4'-fluoro-[1,1'biphenyl]-2-yl)carbamate oxalate, in which the XRPD pattern includes the diffraction peak at diffraction angles 2θ of 16.642±0.2°, 17.839±0.2°, 20.981±0.2°, 21.580±0.2° and 22.701±0.2°.

In one exemplary embodiment of the present invention, there is provided the said form IV of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 8.355±0.2°, 11.415±0.2°, 13.419±0.2°, 13.956±0.2°, 15.619±0.2°, 18.579±0.2°, 23.219±0.2°, 24.720±0.2°, 26.478±0.2°, 27.195±0.2°, 28.143±0.2° and 29.172±0.2°.

In one exemplary embodiment of the present invention, there is provided the said form IV of (R)-(1-methylpyrrolidine-3-yl)methyl(3'-chloro-4'-fluoro-[1,1'-biphenyl]-2-yl)carbamate oxalate, in which the peak position of the XRPD pattern may be substantially the same as the peak position of FIG. 14.

In other exemplary embodiment of the present invention, there is provided the said form IV of (R)-(1-methylpyrrolidine-3-yl)methyl(3'-chloro-4'-fluoro-[1,1'-biphenyl]-2-yl)carbamate oxalate, which has the onset temperature of 120.60° C. (±0.5° C.) and the endothermic peak of 126.88° C. (±0.5° C.) during the DSC analysis, if the heating rate is 20° C./min. More preferably, the DSC endothermic peak may be substantially the same as shown in FIG. 15.

Form V

The present invention provides a form V of (R)-(methylpyrrolidine-3-yl)methyl(3'-chloro-4'-fluoro-[1,1'-biphenyl]-2-yl)carbamate oxalate.

In one exemplary embodiment of the present invention, there is provided the form of (R)-(methylpyrrolidine-3-yl)methyl(3'-chloro-4'-fluoro-[1,1'-biphenyl]-2-yl)carbamate oxalate, in which the XRPD pattern includes at least three diffraction peaks selected from the group consisting of diffraction angles 2θ of 10.925±0.2°, 14.200±0.2° and 21.396±0.2°.

In one exemplary embodiment, there is provided the said form V of (R)-(1-methylpyrrolidine-3-yl)methyl(3'-chloro-4'-fluoro-[1,1'-biphenyl]-2-yl)carbamate oxalate, in which the XRPD pattern includes the diffraction peak at diffraction angles 2θ of 10.925±0.2°, 14.200±0.2°, 20.559±0.2° and 21.396±0.2°.

In one exemplary embodiment of the present invention, there is provided the said form V of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 7.049±0.2°, 8.592±0.2°, 16.081±0.2°, 17.226±0.2°, 17.840±0.2° and 19.565±0.2°.

In another exemplary embodiment, there is provided the said form V of (R)-(1-methylpyrrolidine-3-yl)methyl(3'-chloro-4'-fluoro-[1,1'-biphenyl]-2-yl)carbamate oxalate, which the peak position of the XRPD pattern may be substantially the same peak position of FIG. 16.

Form VI

The present invention provides a form VI of (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the said form VI of (R)-(1-methylpyrrolidine-3-yl)methyl(3'-chloro-4'-fluoro-[1,1'-biphenyl]-2-yl)carbamate oxalate, in which the XRPD pattern includes at least three diffraction peaks selected from the group consisting of diffraction angles 2θ of 10.127±0.2°, 10.893±0.2°, 11.751±0.2° and 17.9784±0.2°.

In one exemplary embodiment, there is provided the said form VI of (R)-(1-methylpyrrolidine-3-yl)methyl(3'-chloro-4'-fluoro-[1,1'-biphenyl]-2-yl)carbamate oxalate, in which the XRPD pattern includes the diffraction peak at diffraction angles 2θ of 10.127±0.2°, 10.893±0.2°, 11.751±0.2° and 17.978±0.2.

In one exemplary embodiment, there is provided the said form VI of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 7.150±0.2°, 14.362±0.2°, 14.654±0.2°, 15.251±0.2° and 16.360±0.2°.

In one exemplary embodiment of the present invention, there is provided the said form VI of (R)-(1-methylpyrrolidine-3-yl)methyl(3'-chloro-4'-fluoro-[1,1'-biphenyl]-2-yl)carbamate oxalate, in which the peak position of the XRPD pattern may be substantially the same as the peak position of FIG. 17.

Form VII

The present invention provides a form VII of (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the said form VII of (R)-(1-methylpyrrolidine-3-yl)methyl(3'-chloro-4'-fluoro-[1,1'-biphenyl]-2-yl)carbamate oxalate, in which the XRPD pattern includes at least three diffraction peaks selected from the group consisting of diffraction angles 2θ of 8.169±0.2°, 8.847±0.2°, 11.071±0.2° and 13.156±0.2°.

In another exemplary embodiment, there is provided the said form VII of (R)-(1-methylpyrrolidine-3-yl)methyl(3'-chloro-4-fluoro-[1,1'-biphenyl]-2-yl)carbamate oxalate, in which the XRPD pattern includes the diffraction peak at diffraction angles 2θ of 8.169±0.2°, 8.847±0.2°, 11.071±0.2° and 13.156±0.2°.

In one exemplary embodiment of the present invention, there is provided the said form VII of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 13.345±0.2°, 14.220±0.2°, 15.828±0.2°, 16.486±0.2° and 17.186±0.2°. Particularly, there is provided the form VII of (R)-(1-methylpyrrolidine-3-yl)methyl(3-chloro-4'-fluoro-[1,1'-biphenyl]-2-yl)carbamate oxalate, in which the peak position of the XRPD pattern may be substantially the same as the peak position of FIG. 18.

Form VIII

The present invention provides a form VIII of (R)-(1-methylpyrrolidine-3-yl)methyl(3'-chloro-4'-fluoro-[1,1'-biphenyl]-2-yl)carbamate oxalate.

In one exemplary embodiment of the present invention, there is provided the said form VIII of (R)-(1-methylpyrrolidine-3-yl)methyl(3'-chloro-4'-fluoro-[1,1'-biphenyl]-2-yl)carbamate oxalate, in which the XRPD pattern includes at least three diffraction peaks selected from the group consisting of diffraction angles 2θ of 8.903±0.2°, 13.090±0.2°, 14.347±0.2° and 15.871±0.2°.

In other exemplary embodiment, there is provided the said form VIII of (R)-(1-methylpyrrolidine-3-yl)methyl(3'-chloro-4'-fluoro-[1,1'-biphenyl]-2-yl)carbamate oxalate, in which the XRPD pattern includes the diffraction peak at diffraction angles 2θ of 8.903±0.2°, 13.090±0.2°, 14.347±0.2° and 15.871±0.2°.

In another exemplary embodiment, there is provided the said form VIII of (R)-(1-methylpyrrolidine-3-yl)methyl(3'-chloro-4'-fluoro-[1,1'-biphenyl]-2-yl)carbamate oxalate, in which the XRPD pattern further includes at least one diffraction peak selected from the group consisting of diffraction angles 2θ of 6.720±0.2°, 10.646±0.2°, 11.683±0.2°, 13.490±0.2° and 17.941±0.2°. Particularly, there is provided the said form VIII of (R)-(1-methylpyrrolidine-3-yl)methyl(3'-chloro-4'-fluoro-[1,1'-biphenyl]-2-yl)carbamate oxalate, in which the peak position of the XRPD pattern may be substantially the same as the peak position of FIG. 19.

Methods for Preparing Forms I to VIII

The present invention provides a method for preparing a form I of (R)-(1-methylpyrrolidine-3-yl)methyl(3'-chloro-4'-fluoro-[1,1'-biphenyl]-2-yl)carbamate oxalate, wherein the method includes steps of: dissolving a free base of (R)-(1-methylpyrrolidine-3-yl)methyl(3'-chloro-4'-fluoro-[1,1'-biphenyl]-2-yl)carbamate in acetone; inserting oxalic acid into the said solution and stirring the resulting mixture; and crystallizing the resulting mixture by means of methyl-t-butyl ether, In another exemplary embodiment of the present invention, the method further includes a step of recrystallizing the, said form I of (R)-(1-methylpyrrolidine-3-yl)methyl(3'-chloro-4'-fluoro-[1,1'-biphenyl]-2-yl)carbamate oxalate by means of an organic solvent.

Particularly, the present invention provides a method for preparing one of forms II to VIII of (R)-(1-methylpyrrolidine-3-yl)methyl(3'-chloro-4'-fluoro-[1,1'-biphenyl]-2-yl)carbamate oxalate, wherein the method includes the step of recrystallizing the form I of (R)-(1-methylpyrrolidine-3-yl)methyl(3'-chloro-4'-fluoro-[1,1'-biphenyl]-2-yl)carbamate oxalate by means of at least one or two solvents selected from the group consisting of an alcohol-based solvent; ether-based solvent; ester-based solvent; ketone-based solvent; halogenated hydrocarbon-based solvent; nitrile-based solvent; and hydrocarbon-based solvent.

More particularly, the present invention provides the method for preparing the form II of (R)-(1-methylpyrrolidine-3-yl)methyl(3'-chloro-4'-fluoro-[1,1'-biphenyl]-2-yl)carbamate oxalate, wherein the method includes the step of recrystallizing the said form I of (R)-(1-methylpyrrolidine-3-yl)methyl(3'-chloro-4'-fluoro-[1,1'-biphenyl]-2-yl)carbamate oxalate by means of a recrystallization solvent selected from the group consisting of dichloromethane; acetone; heptane; methylethylketone; acetonitrile; and a mixture thereof.

In one exemplary embodiment, there is provided the method for preparing the form II of (R)-(1-methylpyrrolidine-3-yl)methyl(3'-chloro-4'-fluoro-[1,1'-biphenyl]-2-yl)carbamate oxalate, in which the step of recrystallizing by means of the said recrystallization solvent may further include a step of inserting the recrystallization solvent and centrifuging the resulting mixture.

Also, the present invention provides a method for preparing the form III of (R)-(1-methylpyrrolidine-3-yl)methyl(3'-chloro-4'-fluoro-[1,1'-biphenyl]-2-yl)carbamate oxalate, wherein the method includes the step of recrystallizing the said form I of (R)-(1-methylpyrrolidine-3-yl)methyl(3'-chloro-4'-fluoro-[1,1'-biphenyl]-2-yl)carbamate oxalate by means of the recrystallization solvent selected from the group consisting of ethanol; methyl-t-butyl ether; heptane; 1,4-dioxane; isopropyl acetate; dichloromethane; isopropanol; and a mixture thereof.

In one exemplary embodiment, there is provided the method for preparing the form III of (R)-(1-methylpyrrolidine-3-yl)methyl(3'-chloro-4'-fluoro-[1,1'-biphenyl]-2-yl)carbamate oxalate, in which the step of recrystallizing by means of the said recrystallization solvent may further include a step of inserting the recrystallization solvent, then, stirring a resulting mixture, and then centrifuging the resulting mixture.

Also, the present invention provides a method for preparing the form IV of (R)-(1-methylpyrrolidine-3-yl)methyl(3'-chloro-4'-fluoro-[1,1'-biphenyl]-2-yl)carbamate oxalate, wherein the method includes the step of recrystallizing the said form I of (R)-(3-methylpyrrolidine-3-yl)methyl(3'-chloro-4'-fluoro-[1,1'-biphenyl]-2-yl)carbamate oxalate by means of 1,4-dioxane.

In one exemplary embodiment, there is provided the method for preparing the form IV of (R)-(1-methylpyrrolidine-3-yl)methyl(3'-chloro-4'-fluoro-[1,1'-biphenyl]-2-yl)carbamate oxalate, in which the step of recrystallizing by means of the said recrystallization solvent may further include the step of inserting the recrystallization solvent and centrifuging the resulting mixture.

In other exemplary embodiment, there is provided a method for preparing the form V of (R)-(1-methylpyrrolidine-3-yl)methyl(3'-chloro-4'-fluoro-[1,1'-biphenyl]-2-yl)carbamate oxalate, wherein the method includes the step of recrystallizing the said form II of (R)-(1-methylpyrrolidine-3-yl)methyl(3'-chloro-4'-fluoro-[1,1'-biphenyl]-2-yl)carbamate oxalate by means of butanol.

In another exemplary embodiment, there is provided a method for preparing the form VI of (R)-(1-methylpyrrolidine-3-yl)methyl(3'-chloro-4'-fluoro-[1,1'-biphenyl]-2-yl)carbamate oxalate, wherein the method includes the step of recrystallizing the said form II of (R)-(1-methylpyrrolidine-3-yl)methyl(3'-chloro-4'-fluoro-[1,1'-biphenyl]-2-yl)carbamate oxalate by means of methanol.

In yet another exemplary embodiment, there is provided a method for preparing the form VII of (R)-(1-methylpyrrolidine-3-yl)methyl(3'-chloro-4'-fluoro-[1,1'-biphenyl]-2-yl)carbamate oxalate, wherein the method includes the step of recrystallizing the said form II of (R)-(1-methylpyrrolidine-3-yl)methyl(3'-chloro-4'-fluoro-[1,1'-biphenyl]-2-yl)carbamate oxalate by means of the recrystallization solvent selected from the group consisting, of ethanol; benzene; and a mixture thereof.

In one exemplary embodiment, there is provided the method for preparing the form VII of (R) (1-methylpyrrolidine-3-yl)methyl(3'-chloro-4'-fluoro-[1,1'-biphenyl]-2-yl)carbamate oxalate, in which the step of recrystallizing by means of the said recrystallization solvent may include a step of sequentially adding the said recrystallization solvents.

In another exemplary embodiment, there is provided a method for preparing the form VIII of (R)-(1-methylpyrrolidine-3-yl)methyl(3'-chloro-4'-fluoro-[1,1'-biphenyl]-2-yl)carbamate oxalate, wherein the method includes the step of recrystallizing the said form II of (R)-(1-methylpyrrolidine-3-yl)methyl(3'-chloro-4'-fluoro-[1,1'-biphenyl]-2-yl)carbamate oxalate by means of the recrystallization solvent selected from the group consisting of ethanol; benzene; and a mixture thereof.

In one exemplary embodiment, there is provided the method for preparing the form VIII of (R)-(1-methylpyrrolidine-3-yl)methyl(3'-chloro-4'-fluoro-[1,1'-biphenyl]-2-yl)carbamate oxalate, in which the step of recrystallizing by means of the said recrystallization solvent may include the step of sequentially adding the said recrystallization solvents.

In the method for preparing the crystal forms above, a type of solvent, a temperature and humidity during dissolution, an order of solvents to be inserted in case of using at least two solvents, a drying temperature, etc., may be adjusted according to a type of crystal form to be obtained.

A Pharmaceutical Composition Containing a Form of (R)-(1-methylpyrrolidine-3-yl)methyl(3'-chloro-4'-fluoro-[1,1'-biphenyl]-2-yl)carbamate oxalate In another exemplary embodiment of the present invention, there is provided a muscarine M3 antagonist containing the above-described (R)-(1-methylpyrrolidine-3-yl)methyl (3'-chloro-4'-fluoro-[1,1'-biphenyl]-2-yl)carbamate oxalate as an effective component.

The said (R)-(1-methylpyrrolidine-3-yl)methyl(3'-chloro-4'-fluoro-[1,1'-biphenyl]-2-yl)carbamate oxalate may be a crystal form, and particularly may be one of the forms I to VIII of (R)-(1-methylpyrrolidine-3-yl)methyl(3'-chloro-4'-fluoro-[1,1'-biphenyl]-2-yl)carbamate oxalate.

In the present invention, the said muscarine M3 receptor antagonist may be a composition for preventing or treating a disease selected from the group of consisting of a chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, hypersalivation syndrome, enuresis, nervous pollakiuria, neurogenic bladder, unstable bladder, cystospasm and pollakisuria.

In one exemplary embodiment of the present invention, the said muscarine M3 antagonist may further include at least one effective component showing the same or similar function in addition to the said (R)-(1-methylpyrrolidine-3-yl)methyl(3'-chloro-4'-fluoro-[1,1'-biphenyl]-2-yl)carbamate oxalate.

Also, in one exemplary embodiment of the present invention, a pharmaceutical composition of the present invention may be prepared for administration by further containing at least one pharmaceutically acceptable carrier in addition to the effective component described above. As the pharmaceutically acceptable carrier, a saline solution, sterilized water, Ringer's solution, buffered saline, dextrose solution, maltodextrin solution, glycerol, ethanol and a mixture of at least one component thereof may be used, and other conventional additives such as an antioxidant, buffer solution, bacteriostatic agent, etc., may he added thereto, if needed. Also, the pharmaceutical composition of the present invention may be formulated into an injectable dosage form such as aqueous solution, suspension, emulsion, etc., pill, capsule, granule or tablet in such a way that a diluent, dispersing agent, surfactant, binder and lubricant are supplementarily added thereto. Furthermore, the pharmaceutical composition of the present invention may be preferably formulated into a preparation according to each disease or component by means of an appropriate method in the art or a method disclosed in Remington's Pharmaceutical Science, Merck Publishing Company, Easton Pa.

In the present invention, the pharmaceutical composition may be orally administered or parenterally administered in a form of injection, suppository, percutaneous agent, inhalant or intravesical injection.

Also, if the muscarine M3 receptor antagonist of the present invention is for oral administration, the (R)-(1-methylpyrrolidine-3-yl)methyl(3'-chloro-4'-fluoro-[1,1'-biphenyl]-2-yl)carbamate oxalate of the present invention may be contained in an amount of 0.1 wt % to 95 wt % in a preparation.

The present invention also provides a method for treating or alleviating a disease caused by a decreased effect of the muscarine M3 receptor in such a way that the muscarine M3 receptor antagonist containing the (R)-(1-methylpyrrolidine-3-yl)methyl(3'chloro-4'-fluoro-[1,1'-biphenyl]-2-yl) carbamate oxalate of the present invention as an effective component is administered into mammals including humans, who require an antagonistic effect of the muscarine M3 receptor.

The muscarine M3 receptor antagonist of the present invention may be used alone or in combination with a surgery, endocrinotherapy, drug treatment and methods of using a biologic response modifier, in order to prevent or treat the disease caused by the decreased effect of the muscarine M3 receptor.

Advantageous Effects

An (R)-(1-methylpyrrolidine-3-yl)methyl(3'-chloro-4'-fluoro-[1,1'-biphenyl]-2-yl)carbamate oxalate provided in the present invention is a crystal form, which has a relatively high melting point and a low hygroscopicity and enables an immediate elution compared to other salt forms of (R)-(1-methylpyrrolidine-3-yl)methyl(3'-chloro-4'-fluoro-[1,1'-biphenyl]-2-yl)carbamate, thus being very suitable to be formulated into a preparation. Also, such oxalate has excellent preservation stability, excellent mechanical stability and liquidity, and uniform particles, thus being very suitable as a parent drug.

Furthermore, a solvent used in a preparation process is inexpensive enough to establish an economical preparation process. Thanks to a simple preparation process, a salt of (R)-(1-methylpyrrolidine-3-yl)methyl(3'-chloro-4'-fluoro-[1,1'-biphenyl]-2-yl)carbamate with a high purity may be prepared at a high yield, thus being suitable for industrial production.

Also, the (R)-(1-methylpyrrolidine-3-yl)methyl(3'-chloro-4'-fluoro-[1,1'-biphenyl]-2-yl)carbamate oxalate has various types of crystal forms, and such polymorphism refers to an origination of different crystal forms of a single compound and an attribute of a complex of several compounds. Such polymorphs are recognized as different solids sharing the same molecular formula, and have unique physicochemical properties such as solubility, melting point, XRPD pattern, etc., and thus may enhance the stability, solubility, etc., of active drugs according to such physiochemical properties, such that the stability and efficacy of drug medicine may be enhanced.

BEST MODE FOR INVENTION

Hereinafter, the present invention will be described in detail through Examples for better understanding of the present invention. However, the following Examples are provided only for the purpose of illustrating the present invention, and thus the scope of the present invention is not limited thereto. The Examples of the present invention are provided to more completely describe the present invention to those having ordinary skill in the art.

<Measurement Method>

A following measurement method is commonly applied to each Example according to the present invention.

1. X-ray Powder Diffraction

X-ray powder diffraction (XRPD) pattern was obtained by means of a solid-phase detector of BRUKER D8 ADVANCE model using CuKα radiation at 1.54178 Å (40 kV, 40 mA). An analysis was performed through measurement at an angle 2θ in a range of 3° to 50° with a step size of 0.02°.

2. Thermal Analysis

A differential scanning calorimetry (DSC) was performed by using METTLER TOLEDO DSC1. A sample weighed in an amount of about 1-10 mg and placed in an aluminum pan with a cover. The said sample was evaluated by using a linear heat lamp of 10°60 C./min or 20° C./min in a range of 30° C. to 350° C.

3. Nuclear Magnetic Resonance (NMR)

A nuclear magnetic resonance (NMR) analysis was performed by using Varian oxford 400 MHz and Agilent 600 MHz.

4. Liquid Chromatography (HPLC)

Detector: Ultraviolet absorptiometer (detection wavelength of 244 nm)

Column: Waters, XBridge C18, 4.6*150 mm, 5 um

Column temperature: 40° C.

Flow: 1.0 mL/min

Injection volume: 10 uL

Mobile phase buffer: A 0.01M $(NH_4)HCO_3$ solution was prepared and adjusted to pH 10.5 by means of ammonia water.

Mobile phase A: Buffer:Acetonitrile=8:2
Mobile phase B: Acetonitrile
Sample solution: 1.0 mg/mL in 50% methanol
Gradient conditions

| Time | Mobile phase A | Mobile phase B |
|------|----------------|----------------|
| 0    | 75             | 25             |
| 20   | 75             | 25             |
| 50   | 25             | 75             |
| 55   | 25             | 75             |
| 55.1 | 75             | 25             |
| 60   | 75             | 25             |

COMPARATIVE EXAMPLE 1

Figure 4:
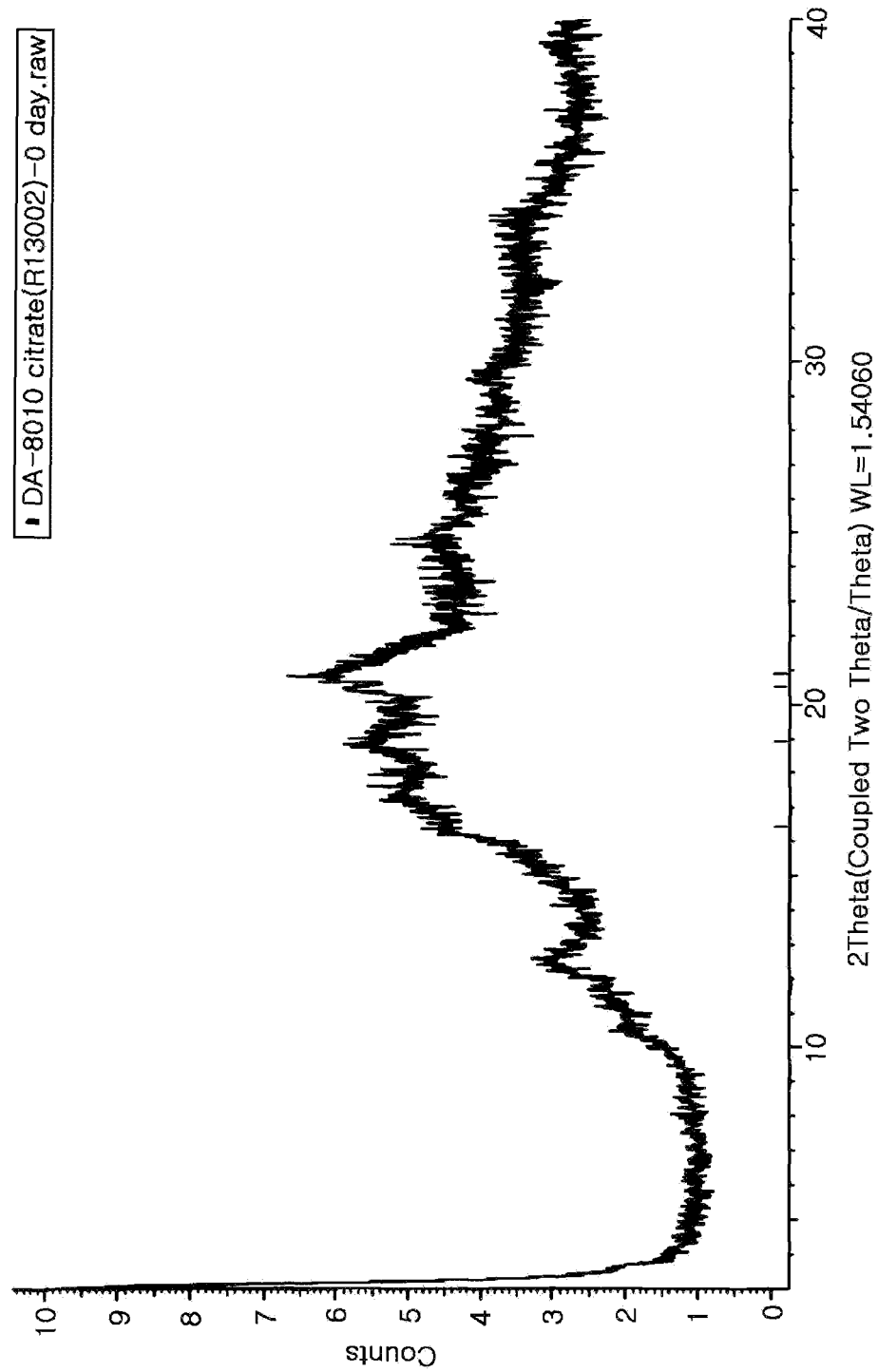
FIG. 4 is a graph of showing the XRPD results of (R)-(1-methylpyrrolidine-3-yl)methyl(3'-chloro-4'-fluoro-[1,1'-biphenyl]-2-yl)carbamate citrate.
Figure 5:
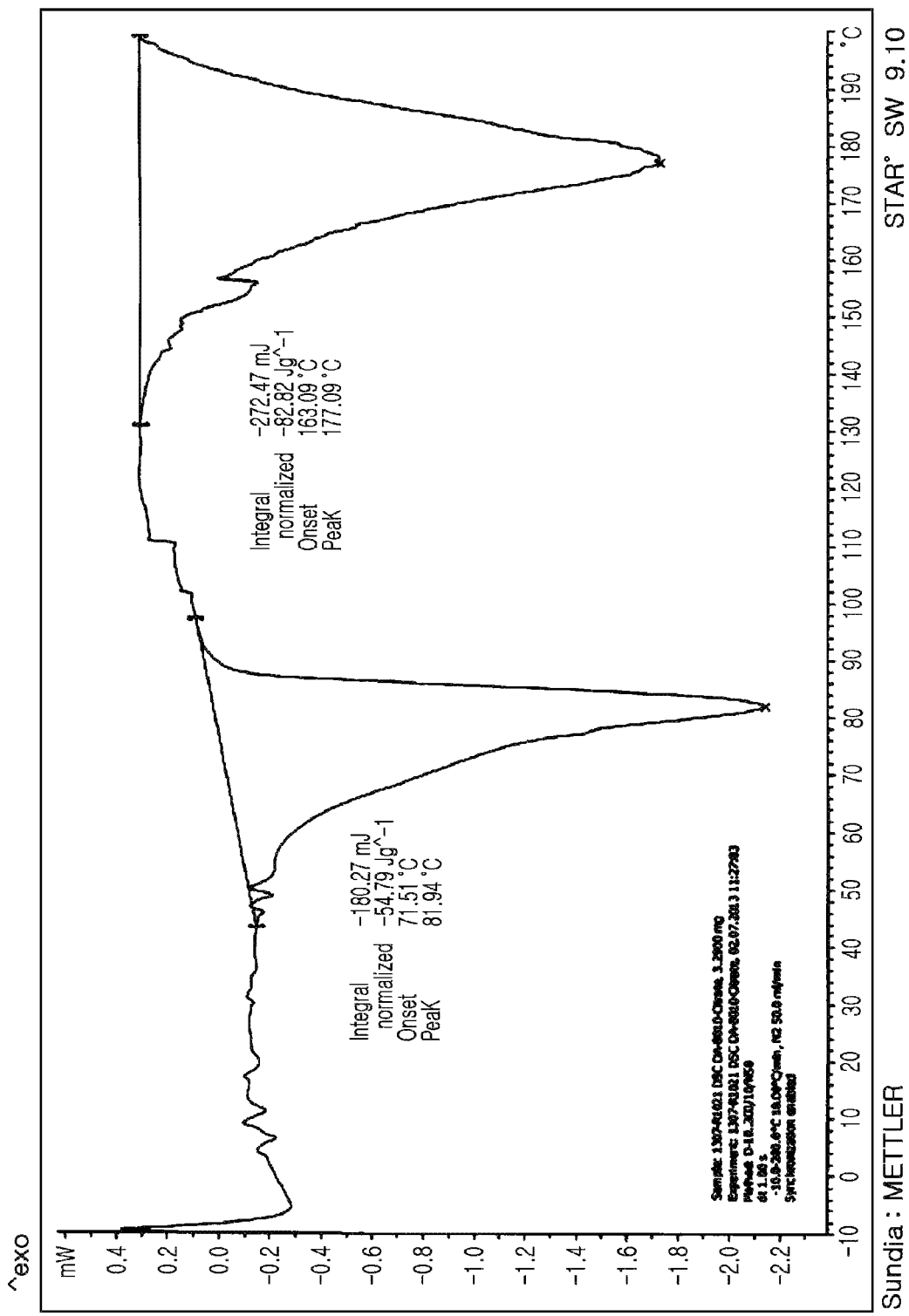
FIG. 5 is a graph of showing the DSC results of (R)-1-methylpyrrolidine-3-yl)methyl(3'-chloro-4'-fluoro-[1,1'-biphenyl]-2-yl)carbamate citrate.
Figure 6:
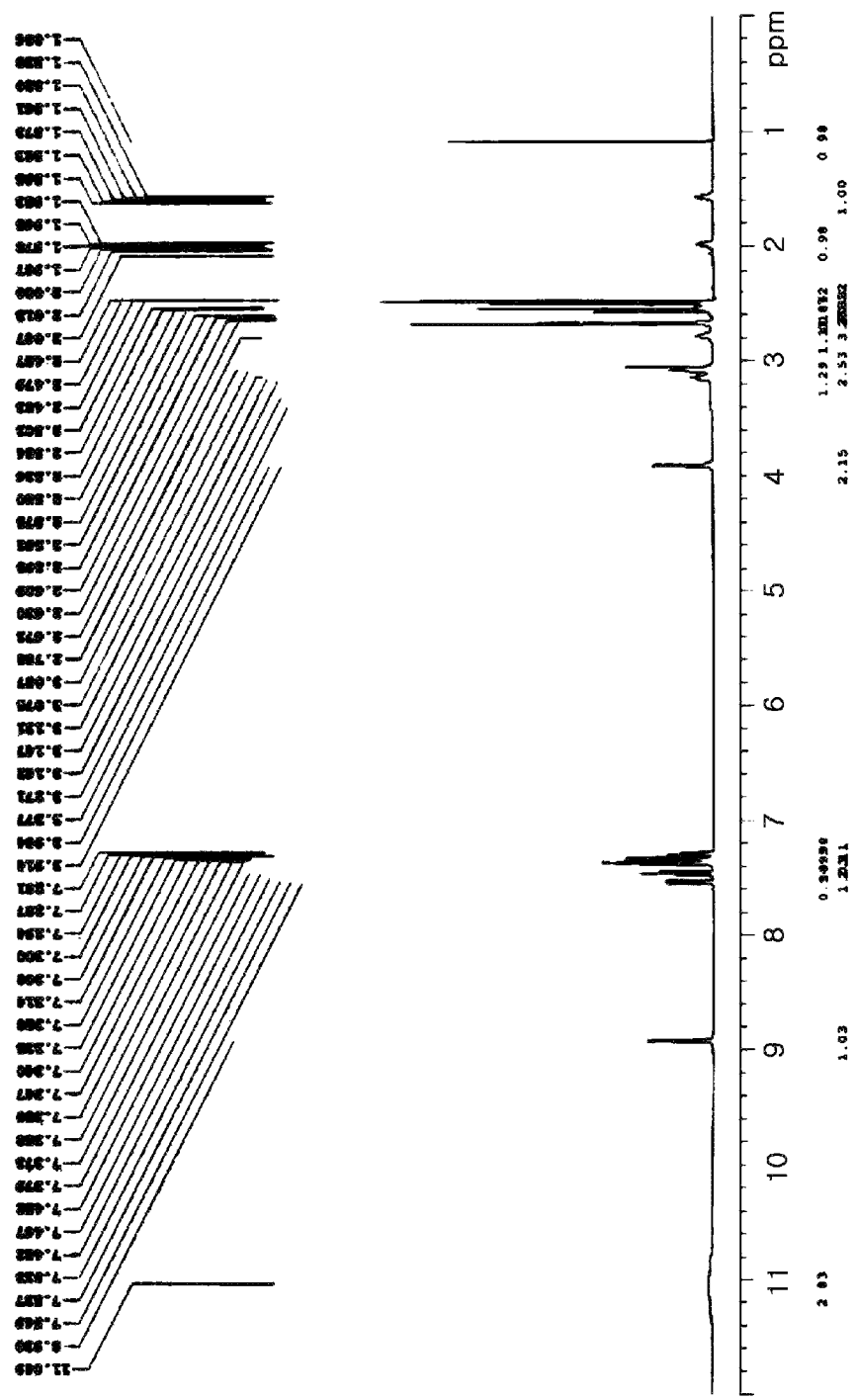
FIG. 6 is a graph of showing the NMR results of (R)-(1-methylpyrrolidine-3-yl)methyl(3'-chloro-4'-fluoro-[1,1'-biphenyl]-2-yl)carbamate citrate.

Preparation of (R)-(1-methylpyrrolidine-3-yl)methyl (3'-chloro-4'-fluoro-[1,1'-biphenyl]-2-yl)carbamate citrate A free base of (R)-(1-methylpyrrolidine-3-yl)methyl(3'-chloro-4'-fluoro-[1,1'-biphenyl]-2-yl)carbamate (0.5 g) was inserted into a reactor, after which acetone (5 mL) was inserted thereinto and dissolved. After that, citric acid (0.27 g) was dissolved in acetone (5 mL) and inserted into the reactor. A resulting mixture was stirred at room temperature for one hour, after which the resulting reactant was concentrated. Methyl-t-butyl ether (40 mL) was added into a resulting concentrate in the reactor and stirred at 0° C. for 12 hours, after which a resulting solid was filtered out, then vacuum-dried at room temperature for four hours, and then analyzed via an HPLC, such that a title compound with a relative purity of 97.7% was obtained. Accordingly, a resulting X-ray powder diffraction (XRPD) pattern was shown in FIG. 4; results of a differential scanning calorimetry (DSC) were shown in FIG. 5; and results of nuclear magnetic resonance (NMR) analysis were shown in FIG. 6.

COMPARATIVE EXAMPLE 2

Figure 7:
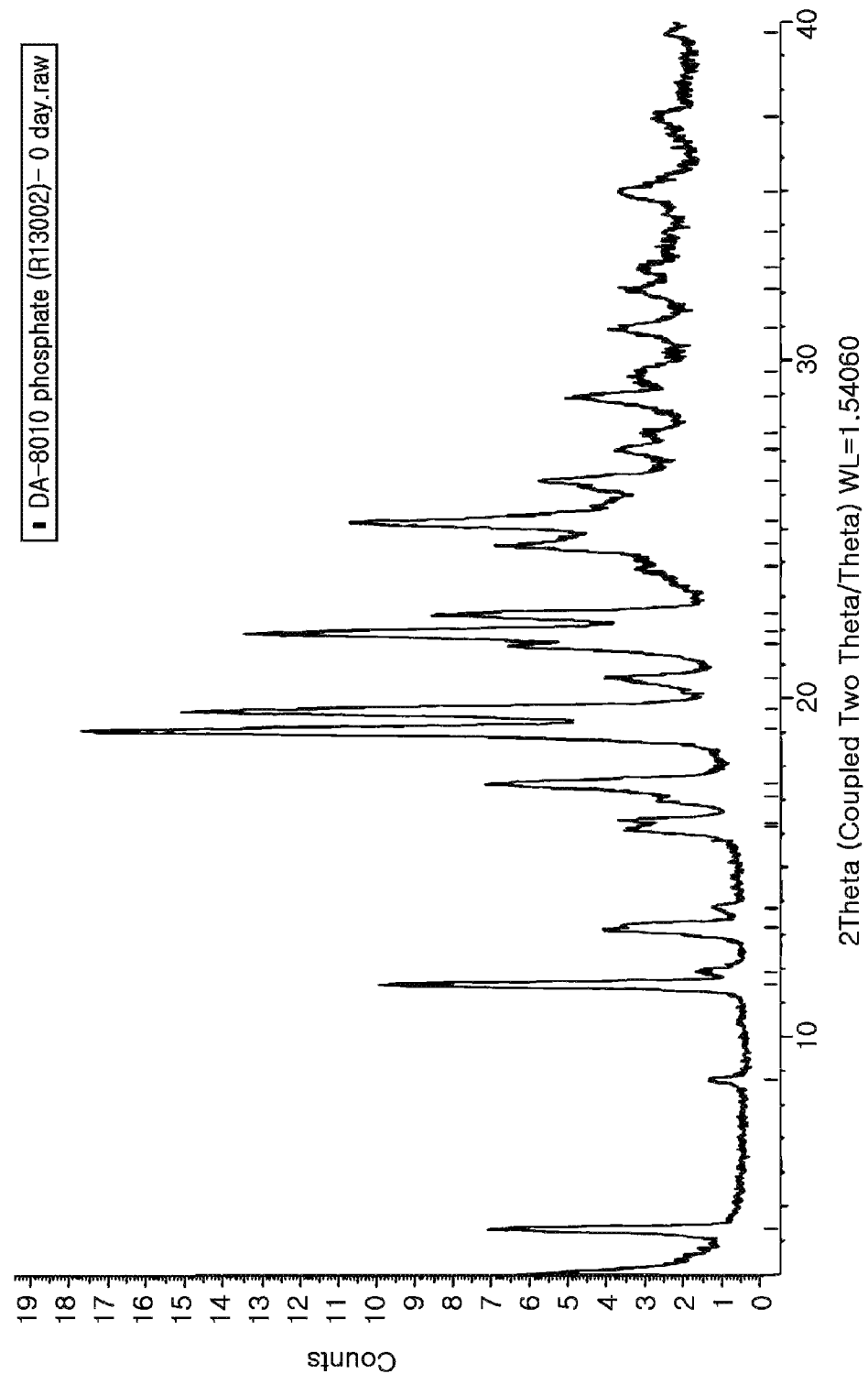
FIG. 7 is a graph of showing the XRFD results of (R)-(1-methylpyrrolidine-3-yl)methyl(3'-chloro-4'-fluoro-[1,1'-biphenyl]-2-yl)carbamate phosphate.
Figure 8:
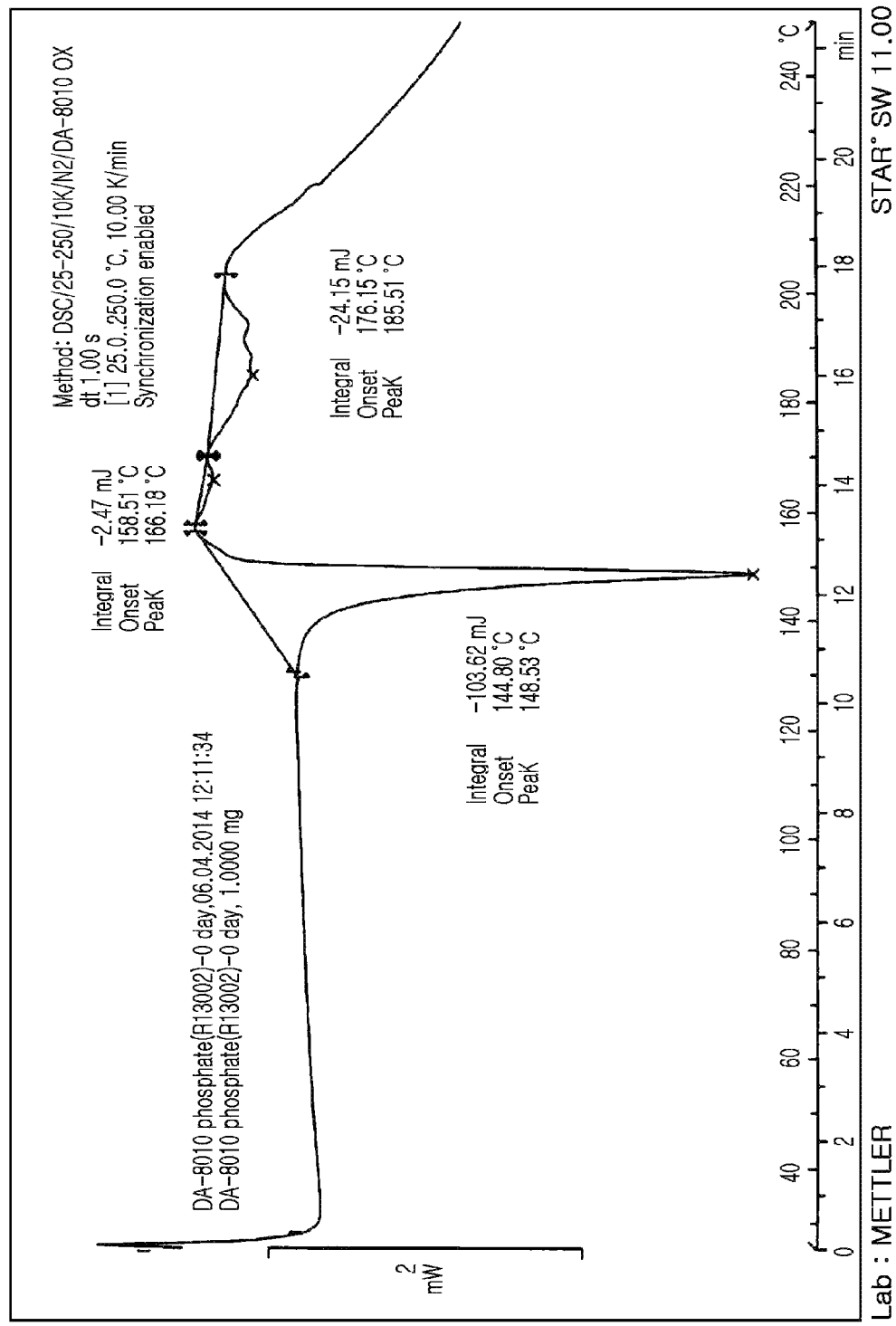
FIG. 8 is a graph of showing the DSC results of (R)-(1-methylpyrrolidine-3-yl)methyl(3'-chloro-4'-fluoro-[1,1'-biphenyl]-2-yl)carbamate phosphate.
Figure 9:
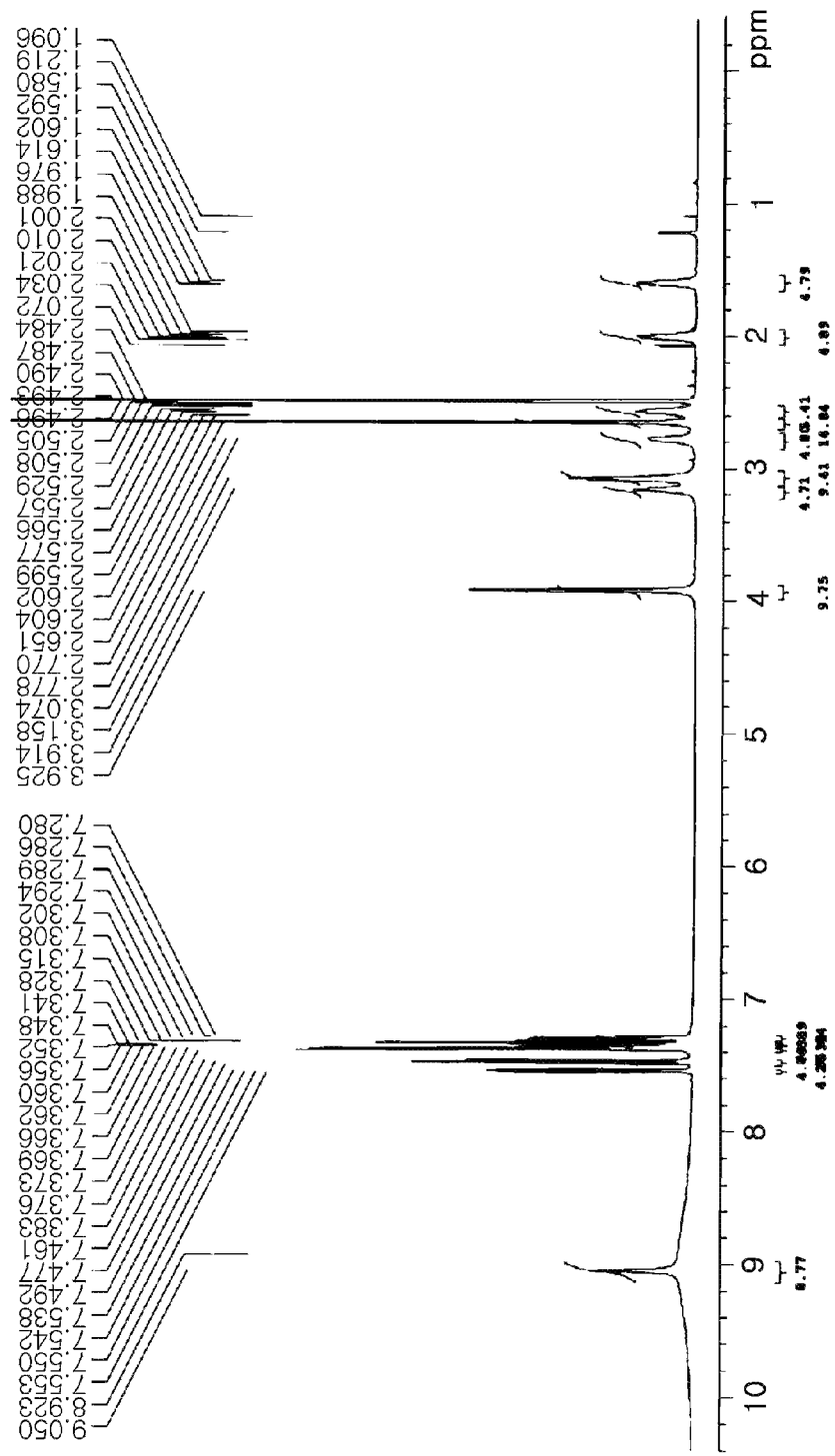
FIG. 9 is a graph of showing the NMR results of (R)-(1-methylpyrrolidine-3-yl)methyl(3'-chloro-4'-fluoro-[1,1'-biphenyl]-2-yl)carbamate phosphate.

Preparation of (R)-1-methylpyrrolidine-3-yl)methyl (3'-chloro-4'-fluoro-[1,1'-biphenyl]-2-yl)carbamate phosphate The free base of (R)-(1-methylpyrrolidine-3-yl)methyl(3'-chloro-4'-fluoro-[1,1'-biphenyl]-2-yl)carbamate (1.0 g) was inserted into the reactor, after which acetone (10 mL) was inserted thereinto and dissolved. After that, phosphoric acid (0.49 g) was inserted into the reactor. Methyl-t-butyl ether (100 mL) was added into the reactor at 0° C. and stirred at 0° C. for 14 hours, after which a resulting solid was filtered out, then vacuum-dried at room temperature for two hours, and then analyzed via the HPLC, such that a title compound with a relative purity of 98.4% was obtained. Accordingly, the resulting XRPD pattern was shown in FIG. 7; the DSC results were shown in FIG. 8; and the NMR analysis results were shown in FIG. 9.

EXAMPLE 1

Figure 1:
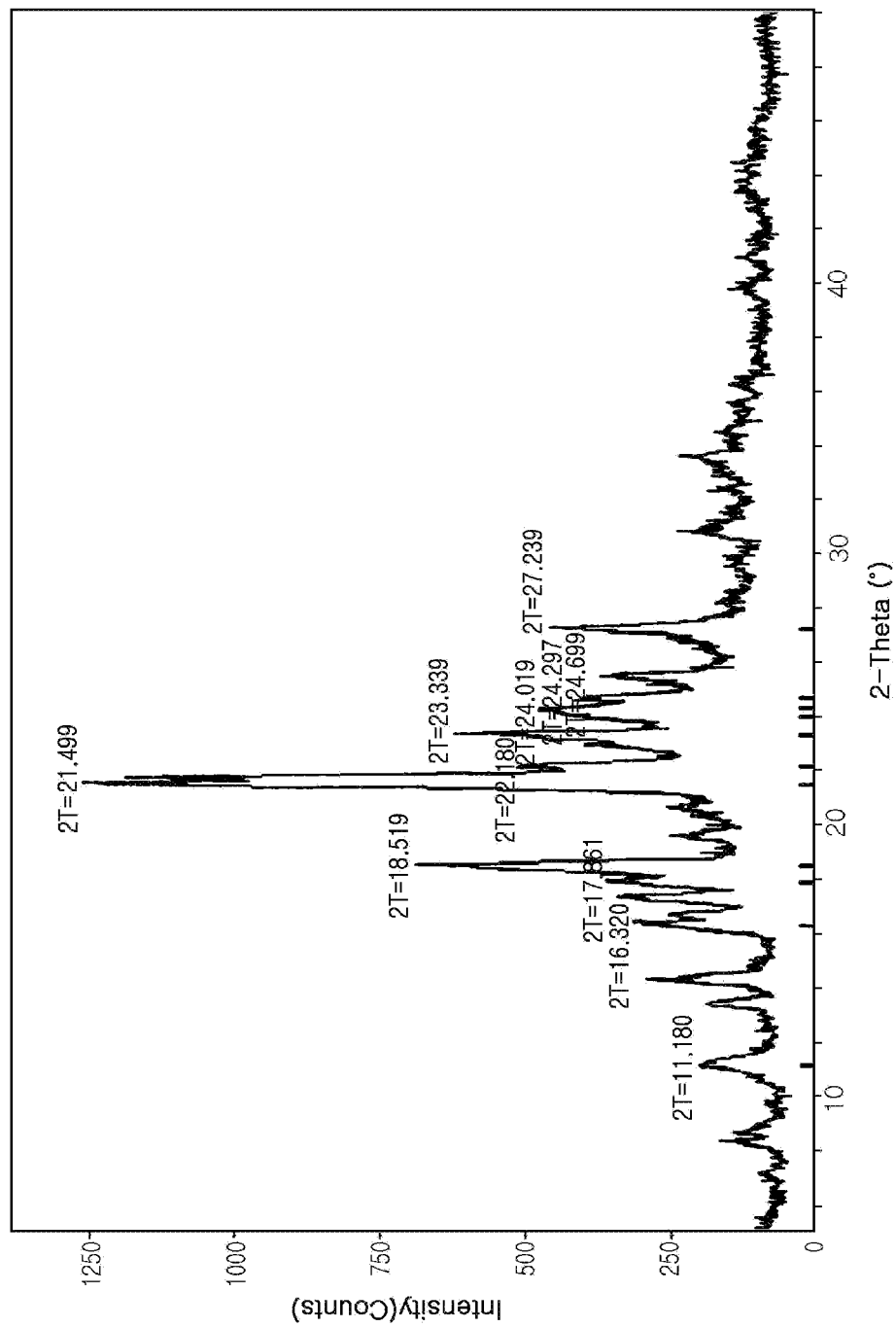
FIG. 1 is a graph of showing results of an X-ray powder diffraction (XRPD) of a form 1 of (R)-(1-methylpyrrolidine-3-yl)methyl(3'-chloro-4'-fluoro-[1,1'-biphenyl]-2-yl)carbamate oxalate.
Figure 2:
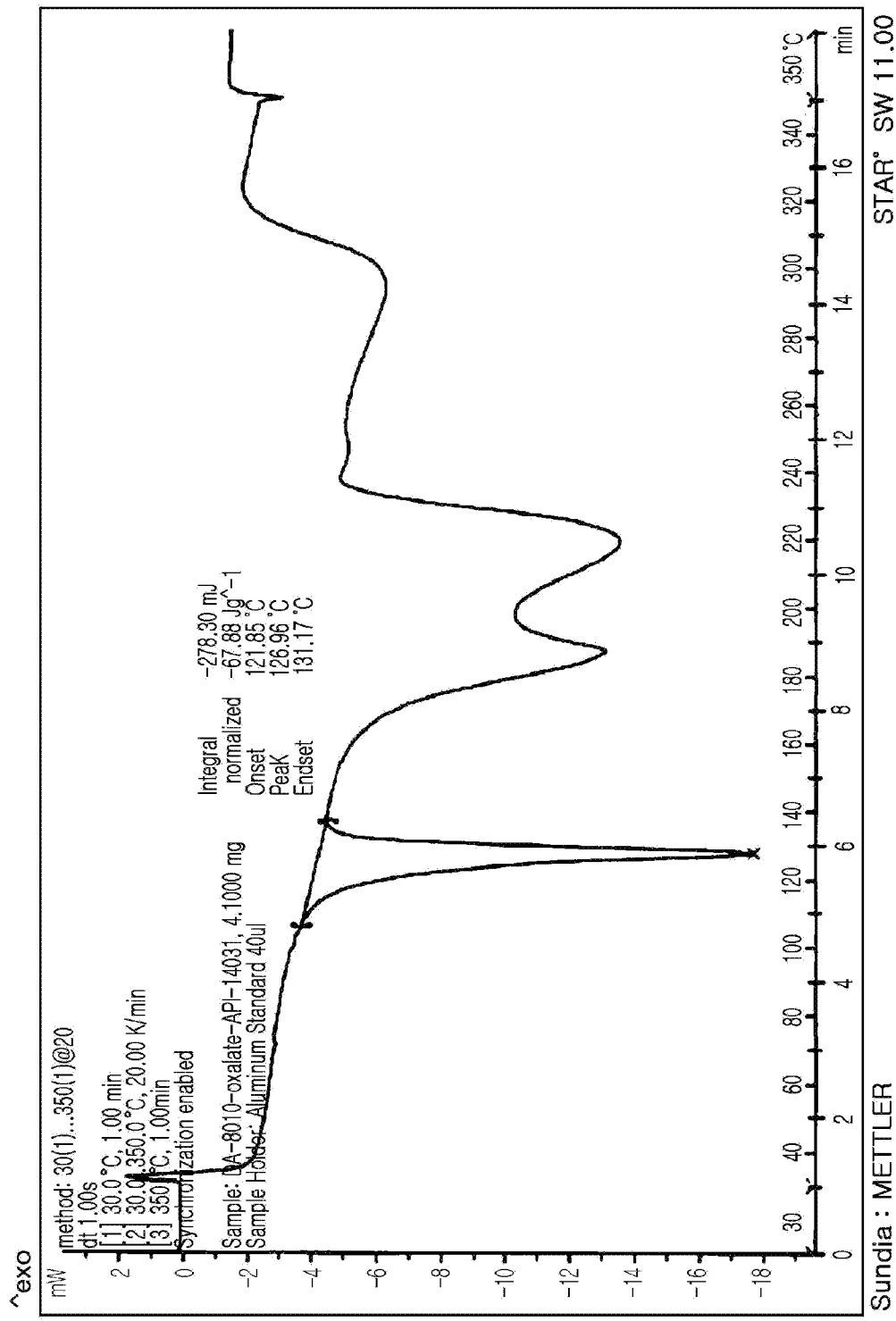
FIG. 2 is a is a graph of showing the results of a differential scanning calorimetry (DSC) of the form I of (R)-(1-methylpyrrolidine-3-yl)methyl(3'-chloro-4'-fluoro-[1,1'-biphenyl]-2-yl)carbamate oxalate.
Figure 3:
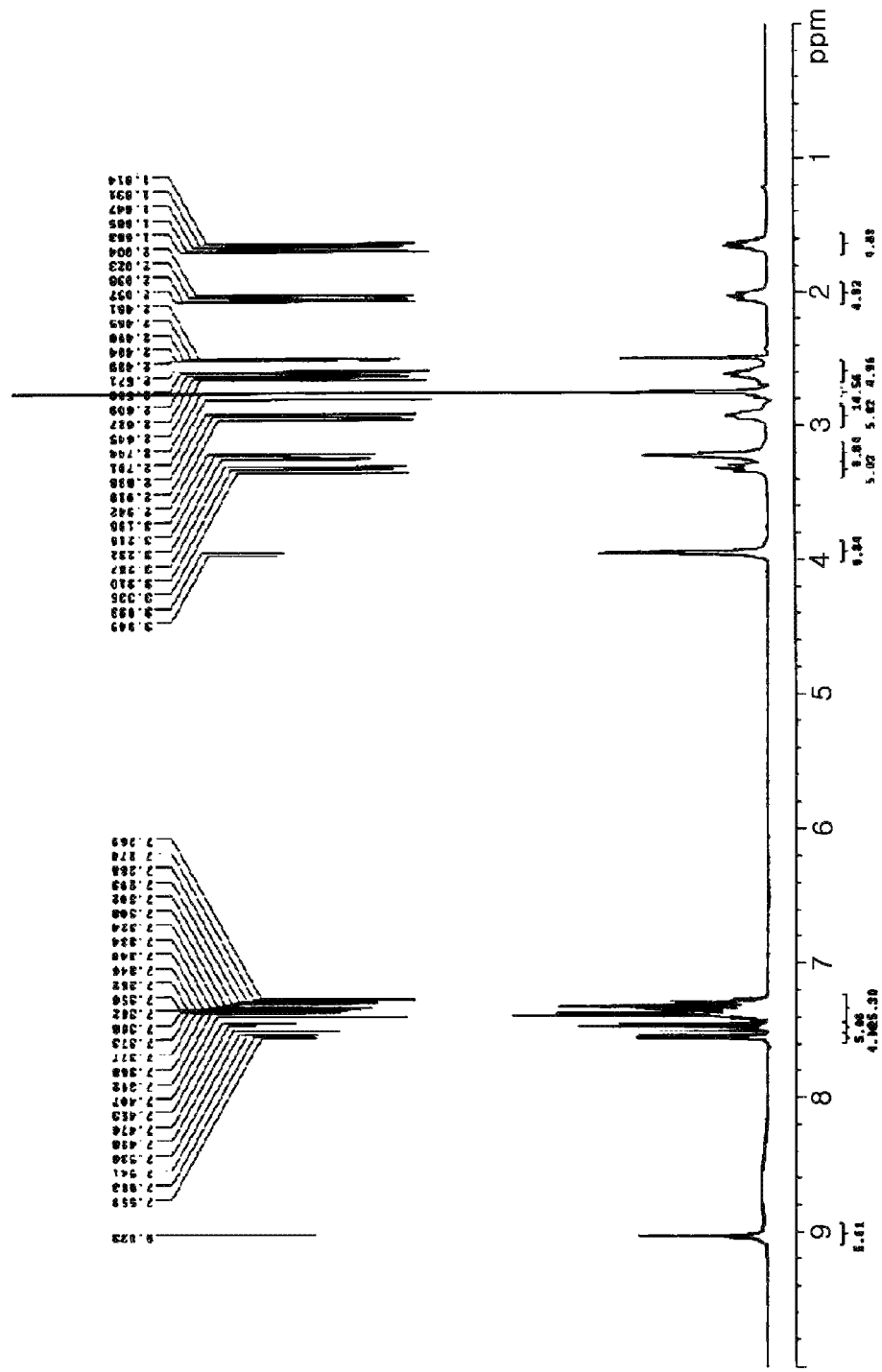
FIG. 3 is a graph of showing the results of a nuclear magnetic resonance (NMR) of the form I of (R)-(1-methylpyrrolidine-3-yl)methyl(3'-chloro-4'-fluoro-[1,1'-biphenyl]-2-yl)carbamate oxalate.

Preparation of (R)-(1-methylpyrrolidine-3-yl)methyl (3'-chloro-4'-fluoro-[1,1'-biphenyl]-2-yl)carbamate oxalate The free base of (R)-(1-methylpyrrolidine-3-yl)methyl(3'-chloro-4'-fluoro-[1,1'-biphenyl]-2-yl)carbamate (0.5 g) was inserted into the reactor, after which acetone (5 mL) was inserted thereinto and dissolved. After that, oxalic acid (0.16 g) was dissolved in acetone (5 mL), then inserted into the reactor, and then stirred at room temperature for one hour. Methyl-t-butyl ether (20 mL) was added into the reactor and stirred for six hours, after which a resulting solid was filtered out, then vacuum-dried at room temperature for six hours, and then analyzed via the HPLC, such that a title compound with a relative purity of 99.3% was obtained. Accordingly, the resulting XRPD pattern was shown in FIG. 1; the DSC results were shown in FIG. 2; and the NMR analysis results were shown in FIG. 3.

EXAMPLE 2

Preparation of a Form I of (R)-(1-methylpyrrolidine-3-yl)methyl(3'-chloro-4'-fluoro-[1,1'-biphenyl]-2-yl)carbamate oxalate A form I compound of (R)-(1-methylpyrrolidine-3-yl)methyl(3'-chloro-4'-fluoro-[1,1'-biphenyl]-2-yl)carbamate oxalate was obtained by means of the method of Example 1. Accordingly, the resulting XRPD pattern was shown in FIG. 1; the DSC results were shown in FIG. 2; and the NMR analysis results were shown in FIG. 3.

EXAMPLE 3

Figure 10:
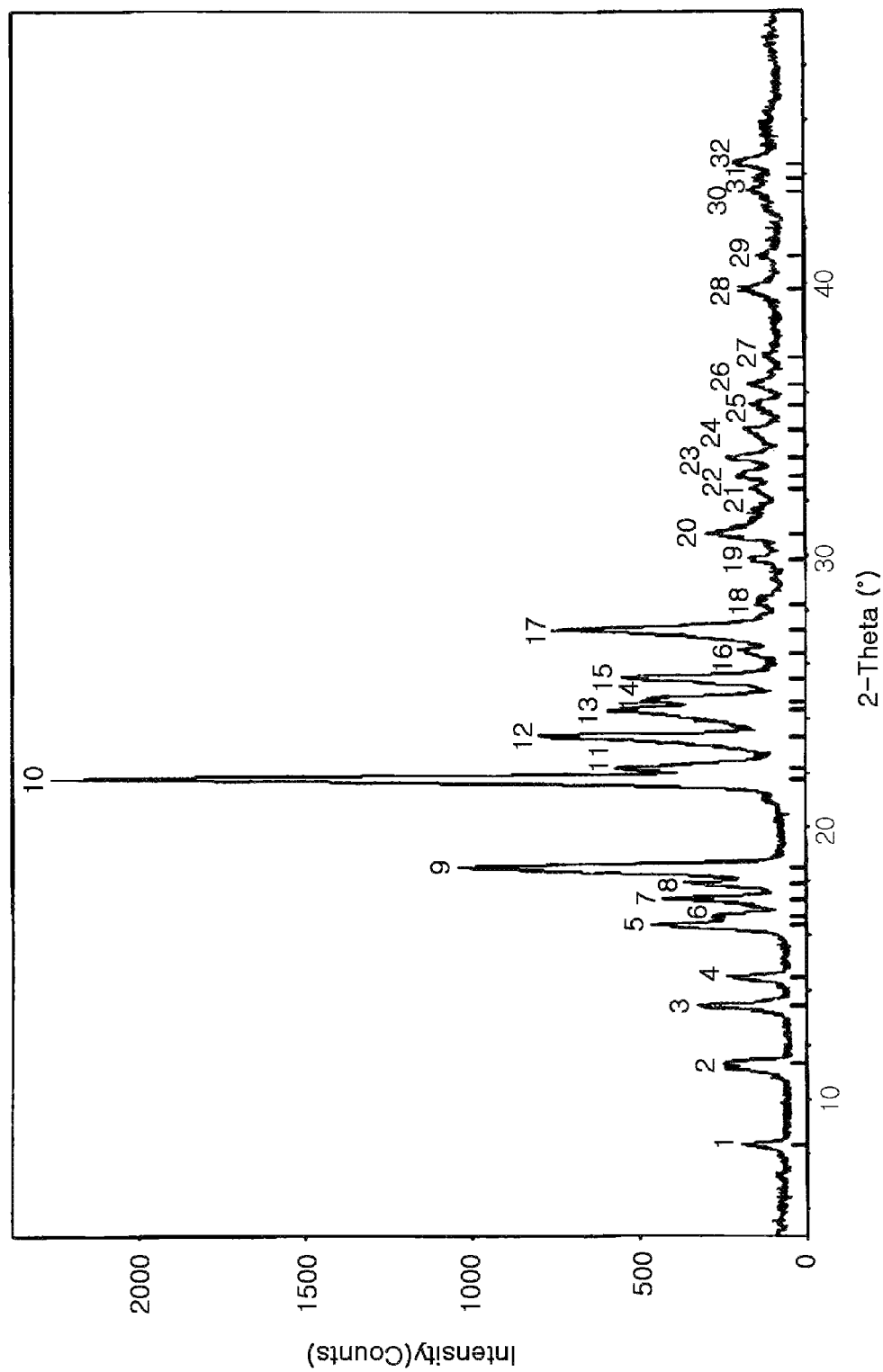
FIG. 10 is a graph of showing the XRPD results, of a form II of (R)-(1-methylpyrrolidine-3-yl)methyl(3'-chloro-4'-fluoro-[1,1'-biphenyl]-2-yl)carbamate oxalate.
Figure 11:
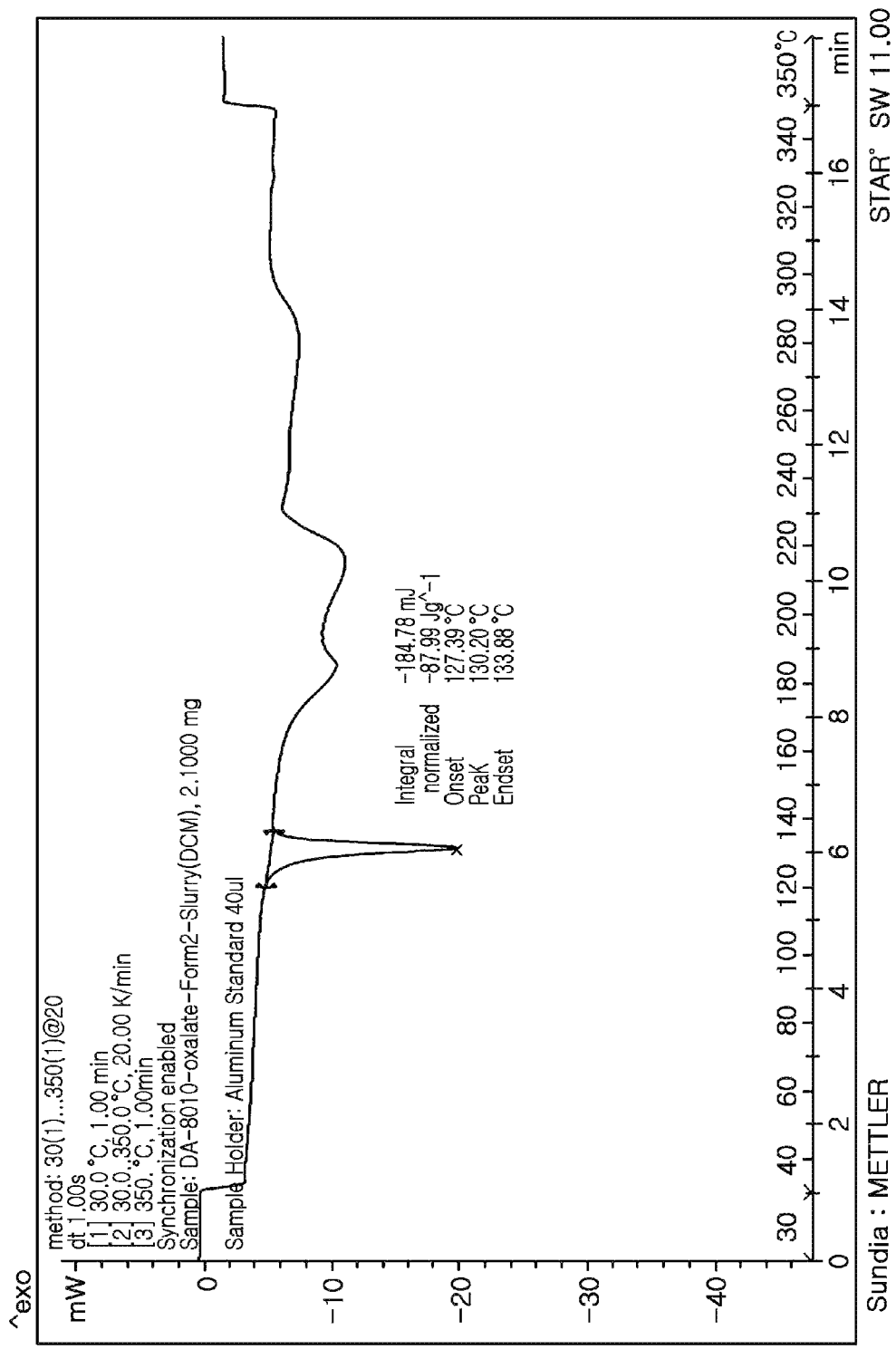
FIG. 11 is a graph of showing the DSC results of the form II of (R)-(1-methylpyrrolidine-3-yl)methyl(3'-chloro-4'-fluoro-[1,1'-biphenyl]-2-yl)carbamate oxalate.

Preparation of a Form II of (R)-(1-methylpyrrolidine-3-yl)methyl(3'-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (50 mg) was inserted into dichloromethane (1 mL), then stirred at room temperature for three days, then centrifuged, and then dried at 40° C., such that a form II was prepared. Accordingly, the resulting XRPD pattern was shown in FIG. 10 and the DSC results were shown in FIG. 11.

EXAMPLE 4

Preparation of the Form II of (R)-(1-methylpyrrolidine-3-yl)methyl(3'-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (40 mg) was dissolved in acetone (2 mL), after which heptane (2 mL) was inserted thereinto. A resulting mixture was stirred at room temperature for 24 hours, then centrifuged, and then dried at 40° C., such that the form II was prepared.

EXAMPLE 5

Preparation of the Form of (R)-(1-methylpyrrolidine-3-yl)methyl(3'-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (50 mg) was inserted into acetone (0.6 mL), and then completed dissolved at 60° C. After dissolution, a resulting mixture was cooled down at room temperature, after which a resulting crystal was centrifuged, and then dried at 40° C., such that the form II was prepared.

EXAMPLE 6

Preparation of the Form II of (R)-(1-methylpyrrolidine-3-yl)methyl(3'-chloro-4'-fluoro-[1,1'-biphenyl]-2-yl)carbamate oxalate The form II was prepared by using methylethylketone instead of acetone by means of the same method as shown in Example 5.

EXAMPLE 7

Preparation of the Form II of (R)-(1-methylpyrrolidine-3-yl)methyl(3'-chloro-4'-fluoro-[1,1'-biphenyl]-2-yl)carbamate oxalate The form II was prepared by using acetonitrile instead of acetone by means of the same method as shown Example 5.

EXAMPLE 8

Preparation of the Form II of (R)-(1-methylpyrrolidine-3-yl)methyl(3'-chloro-4'-fluoro-[1,1'-biphenyl]-2-yl)carbamate oxalate The form II was prepared by using acetone instead of dichloromethane by means of the same method as shown in Example 3.

EXAMPLE 9

Figure 12:
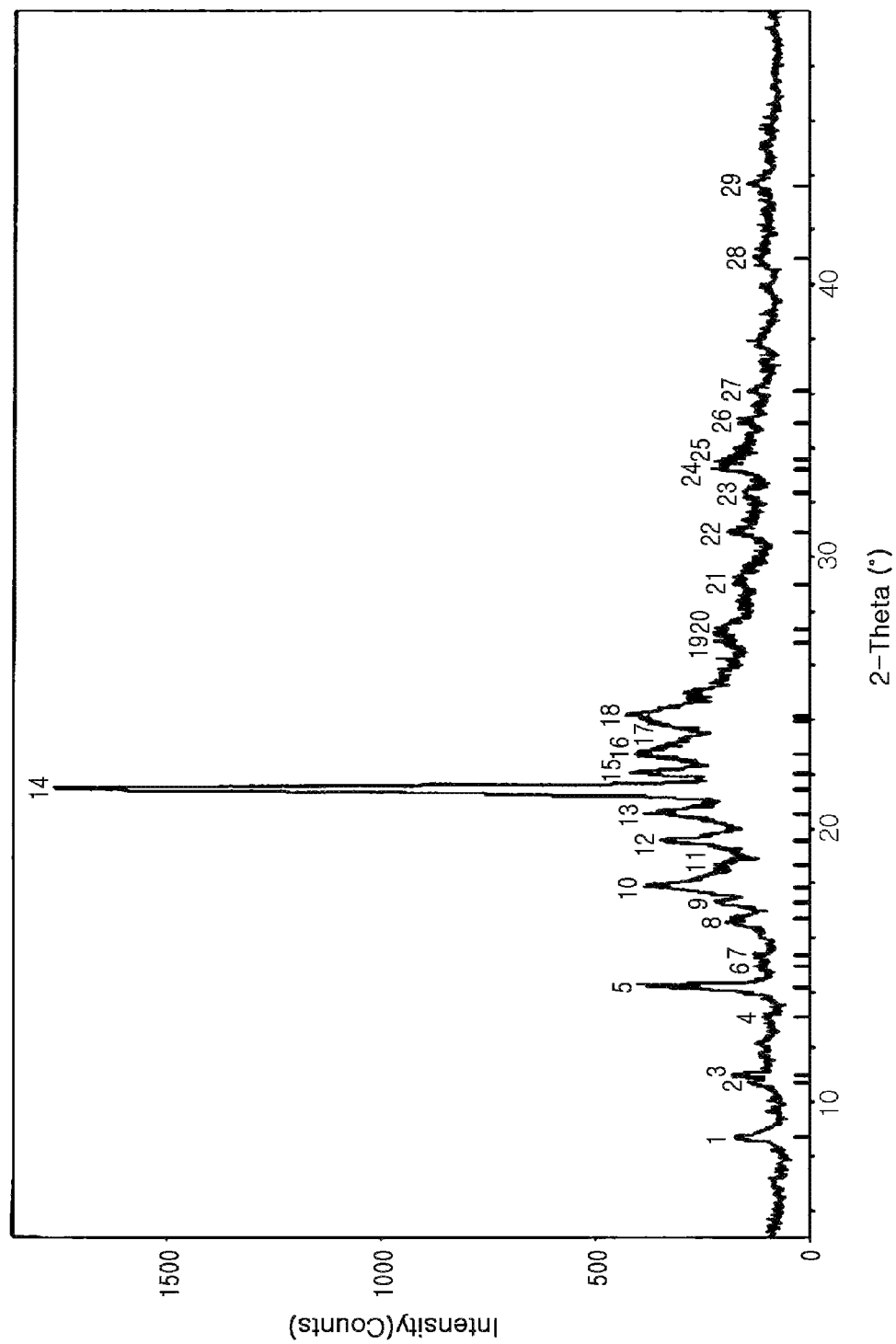
FIG. 12 is a graph of showing the XRPD results of a form III of (R)-(1-methylpyrrolidine-3-yl)methyl(3'-chloro-4'-fluoro-[1,1'-biphenyl]-2-yl)carbamate oxalate.
Figure 13:
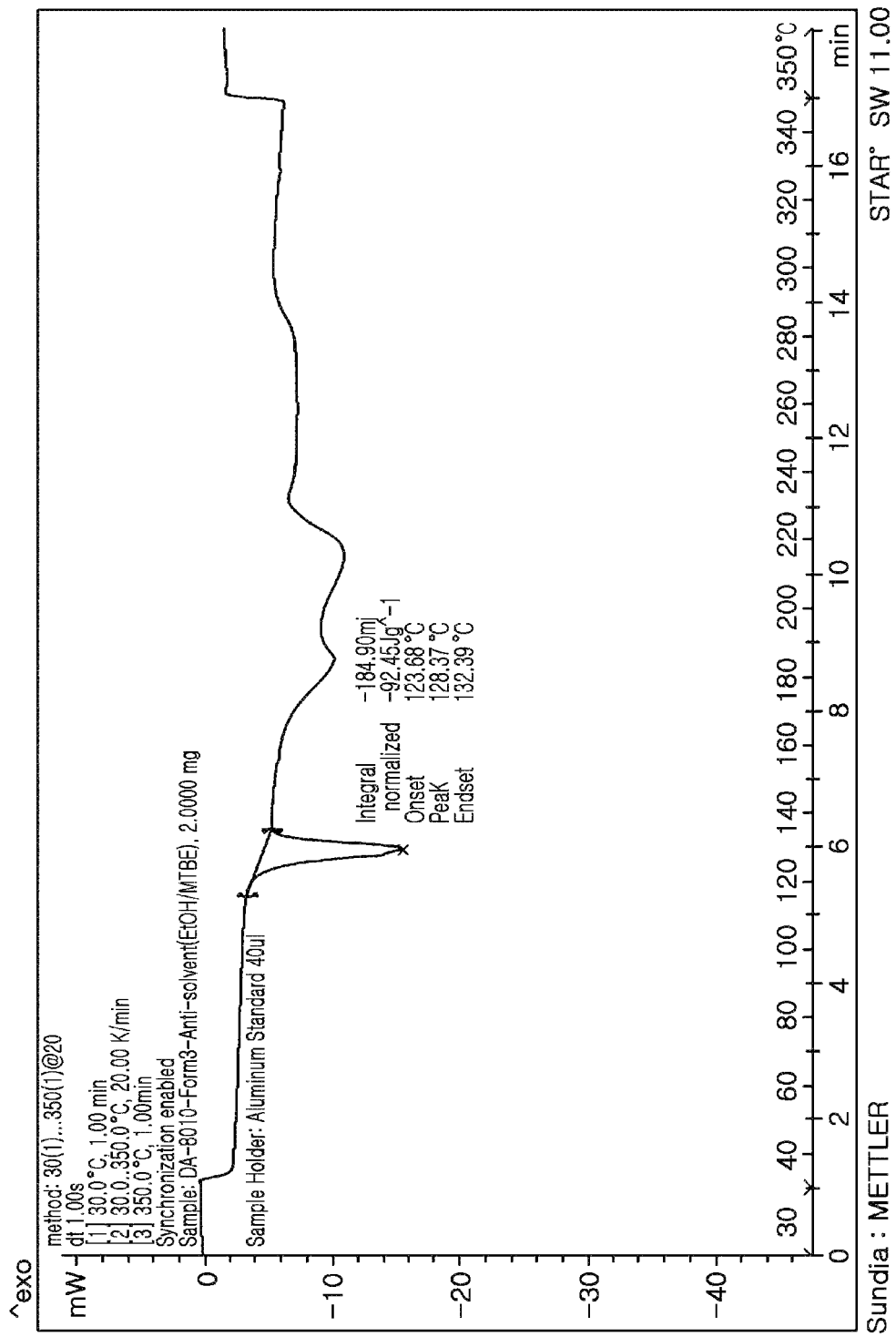
FIG. 13 is a graph of showing the DSC results of the form III of (R)-(1-methylpyrrolidine-3-yl)methyl(3'-chloro-4'-fluoro-[1,1'-biphenyl]-2-yl)carbamate oxalate.

Preparation of a Form III of (R)-(1-methylpyrrolidine-3-yl)methyl(3'-chloro-4'-fluoro-[1,1'-biphenyl]yl)carbamate oxalate The form I of (R)-(1-methylpyrrolidine-3-yl)methyl(3'-chloro)-4'-fluoro-[1,1'-biphenyl]-2-carbamate oxalate (40 mg) was dissolved ethanol (1 mL), after which methyl-t-butyl ether (2 mL) was inserted thereinto. A resulting mixture was stirred at room temperature for one hour, then centrifuged, and then dried at 40° C., such that a form III was prepared. Accordingly, the resulting XRPD pattern was shown in FIG. 12 and the DSC results were shown FIG. 13.

EXAMPLE 10

Preparation of the Form II of (R)-(1-methylpyrrolidine-3-yl)methyl(3'-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (40 mg) was dissolved in ethanol (1 mL), after which haptane (1 mL) was inserted thereinto. A resulting mixture was stirred at room temperature for one hour, then centrifuged, and then dried at 40° C., such that the form III was prepared.

EXAMPLE 11

Preparation of the Form III of (R)-(1-methylpyrrolidine-3-yl)methyl(3'-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (40 mg) was dissolved in 1,4-dioxane (1.7 mL), after which isopropyl acetate (15.3 mL) was inserted thereinto. A resulting mixture was stirred at room temperature for 24 hours, then centrifuged, and then dried at 40° C., such that the form III was prepared.

EXAMPLE 12

Preparation of the Form III of (R)-(1-methylpyrrolidine-3-yl)methyl(3-chloro-4'-fluoro-[1,1'-biphenyl]-2-yl)carbamate oxalate The form I of (R)-(1-methylpyrrolidine-3-yl)methyl(3'-chloro-4'-fluoro-[1,1'-biphenyl]-2-yl)carbamate oxalate (40 mg) was dissolved in dichloromethane (2 mL), after which isopropyl acetate (2 mL) was inserted thereinto. A resulting mixture was stirred at room temperature for 1 hour, then centrifuged, and then dried at 40° C., such that the form III was prepared.

EXAMPLE 13

Preparation of the Form III of (R)-(1-methylpyrrolidine-3-yl)methyl(3'-chloro-4'-fluoro-[1,1'-biphenyl]-2-yl)carbamate oxalate The form III was prepared by using isopropanol instead of acetone by means of the same method as shown in Example 5.

EXAMPLE 14

Figure 14:
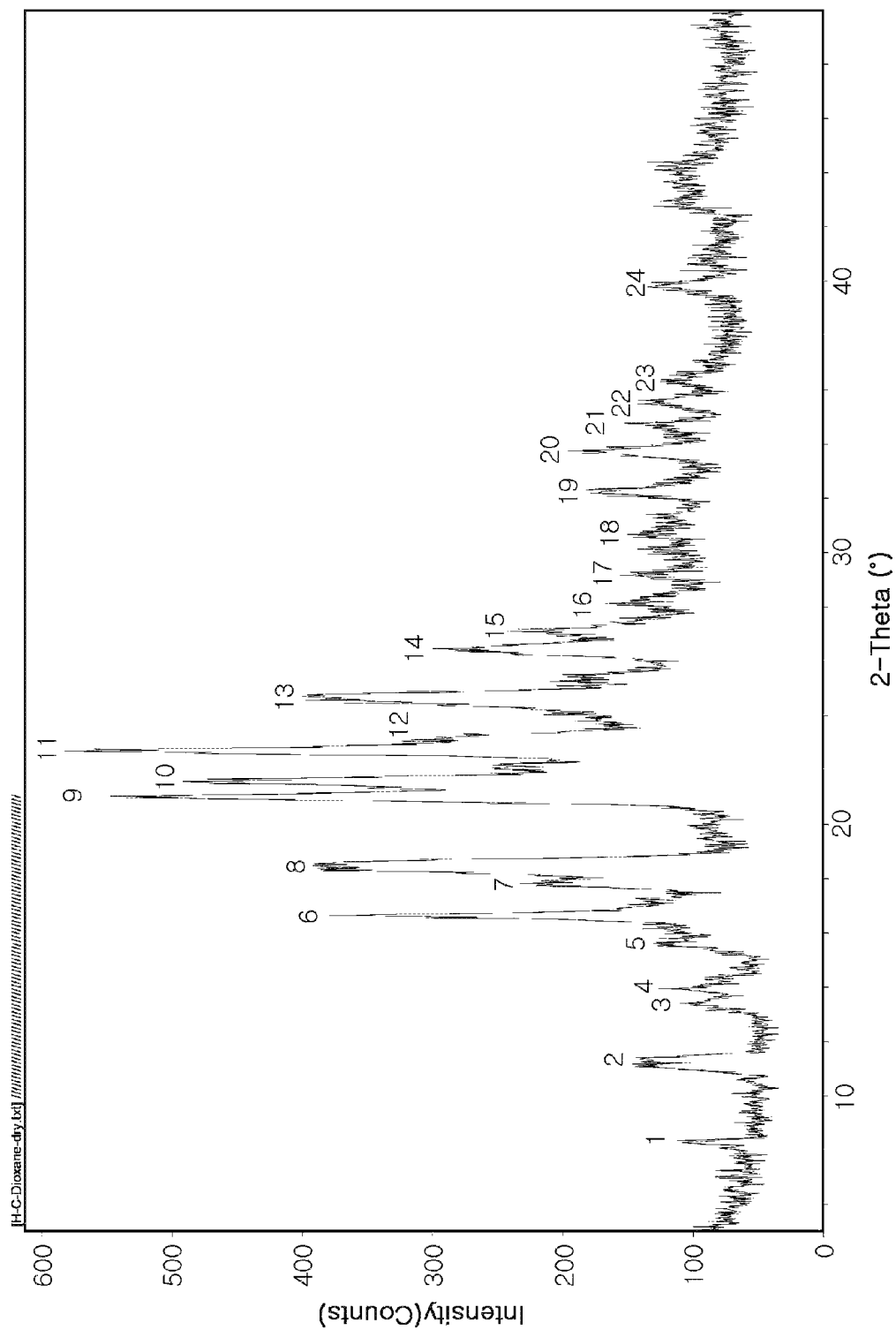
FIG. 14 is a graph of showing the XRPD results of a form IV of (R)-(1-methylpyrrolidine-3-yl)methyl(3'-chloro-4'-fluoro-[1,1'-biphenyl]-2-yl)carbamate oxalate.
Figure 15:
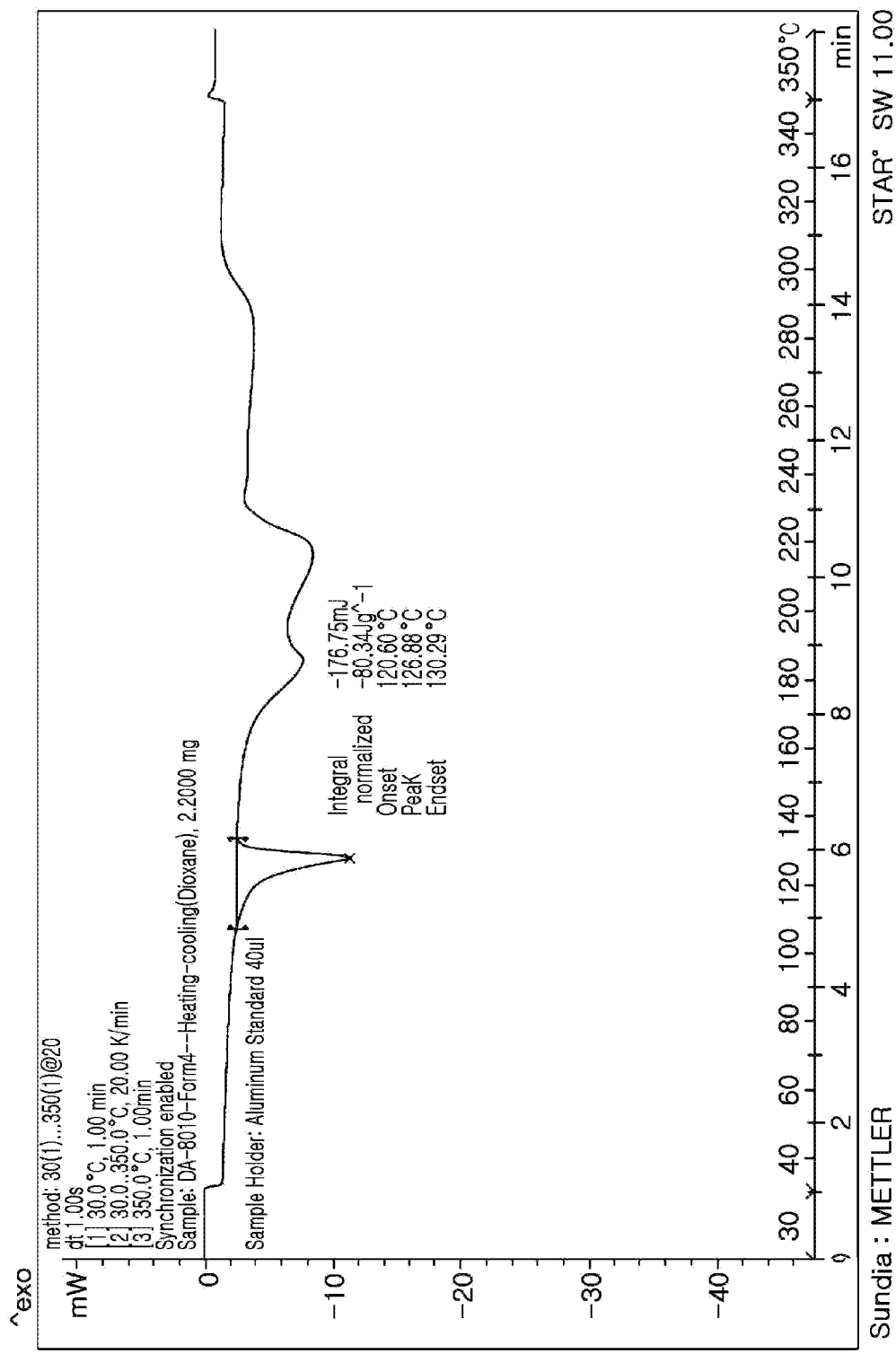
FIG. 15 is a graph of showing the DSC results of the form IV of (R)-(1-methylpyrrolidine-3-yl)methyl(3'-chloro-4'-fluoro-[1,1'-biphenyl]-2-carbamate oxalate.

Preparation of a Form IV of (R)-(1-methylpyrrolidine-3-yl)methyl(3'-chloro-4'-fluoro-[1,1'-biphenyl]-2-yl)carbamate oxalate A form IV was prepared by using 1,4-dioxane instead of acetone by means of the same method as shown in Example 5. Accordingly, the resulting XRPD pattern was shown in FIG. 14 and the DSC results were shown in FIG. 15.

EXAMPLE 15

Figure 16:
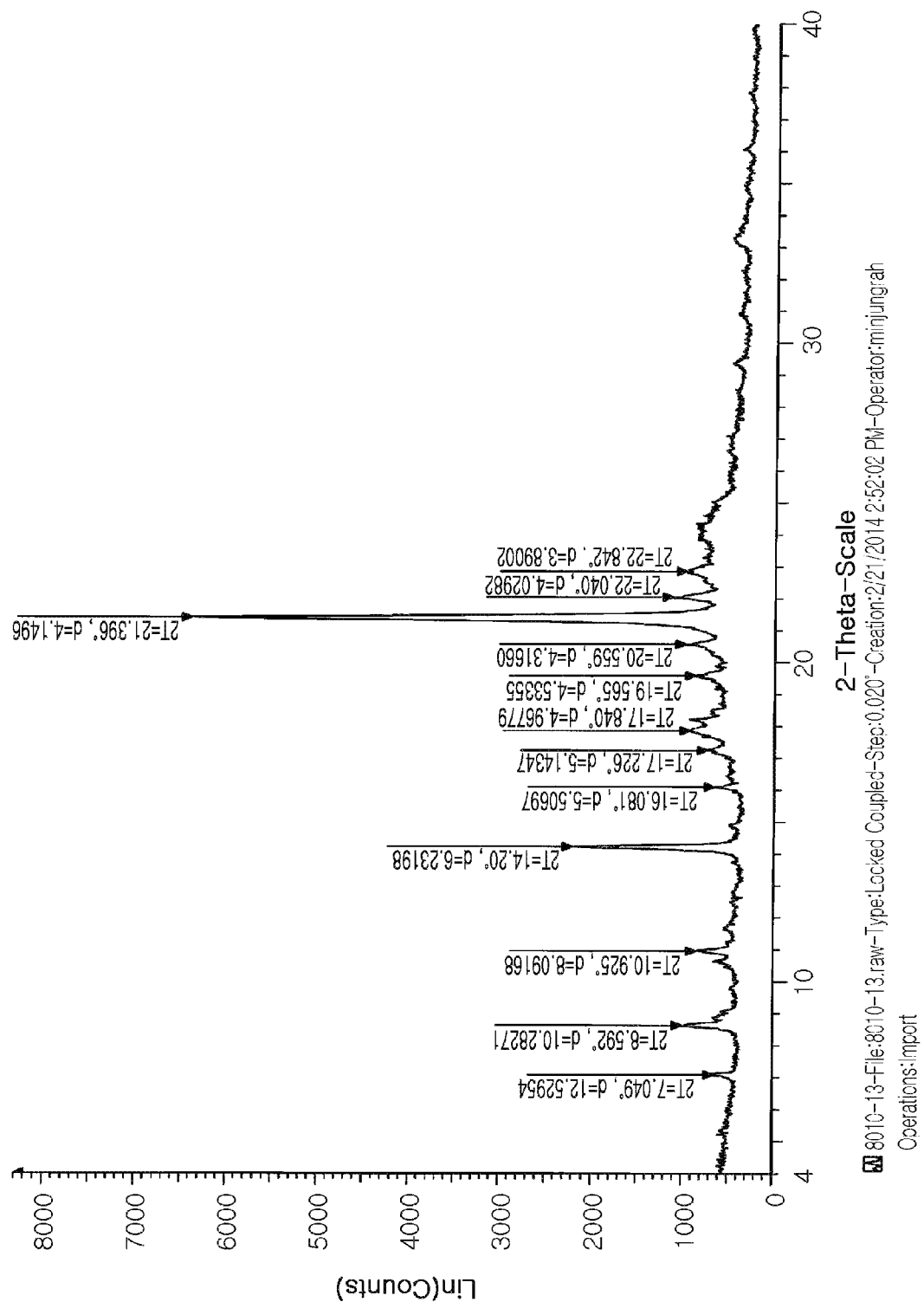
FIG. 16 is a graph of showing the XRPD results of a form V of (R)-(1-methylpyrrolidine-3-yl)methyl(3'-chloro-4'-fluoro-[1,1'-biphenyl]-2-yl)carbamate oxalate.

Preparation of a Form V of (R)-(1-methylpyrrolidine-3-yl)methyl(3'-chloro-4'-fluoro-[1,1'-biphenyl]-2-yl)carbamate oxalate The form II of (R)-(1-methylpyrrolidine-3-yl)methyl(3'-chloro-4'-fluoro-[1,1'-biphenyl]-2-yl)carbamate oxalate (1.1139 g) was dissolved in butanol (100 mL) at a humidity of 31%, and then heated and dissolved up to 45° C. while being stirred. An undissolved crystal was filtered out, and then a filtrate was kept at room temperature. If a resulting solvent was evaporated to produce a crystal, the crystal was moved into a silica gel desiccator, then left alone for about one month, and then completely dried, such that a form V of (R)-(1-methylpyrrolidine-3-yl)methyl(3'-chloro-4'-fluoro-[1,1'-biphenyl]-2-yl)carbamate oxalate was prepared. Accordingly, the resulting XRPD pattern was shown in FIG. 16.

EXAMPLE 16

Figure 17:
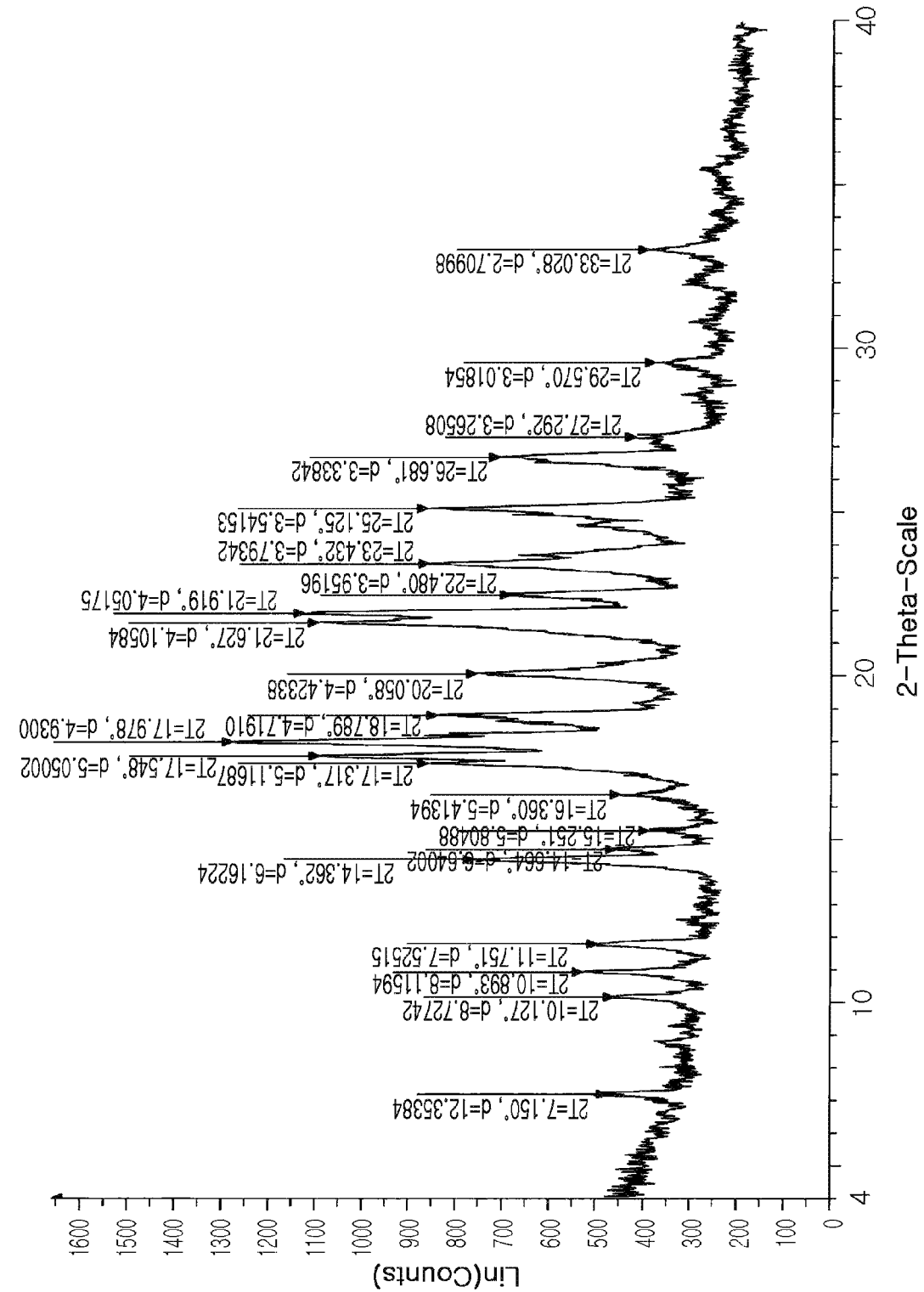
FIG. 17 is a graph of showing the XRPD results of a form VI of (R)-(1-methylpyrrolidine-3-yl)methyl(3'-chloro-4'-fluoro-[1,1'-biphenyl]-2-yl)carbamate oxalate.

Preparation of a Form VI of (R)-(1-methylpyrrolidine-3-yl)methyl(3'-chloro-4'-fluoro-[1,1'-biphenyl]yl)carbamate oxalate The form II of (R)-(1-methylpyrrolidine-3-yl)methyl(3'-chloro-4'-fluoro-[1,1'-biphenyl]-2-yl)carbamate oxalate (2.2356 g) was dissolved in methanol (100 mL), and then heated and dissolved up to 45° C. while being stirred. An undissolved crystal was filtered out, and then a filtrate was kept in a refrigerator (−20° C.) for about three months. After that, the resulting filtrate was moved into the silica gel desiccator at room temperature, then left alone for about nine months, and then dried, such that a form VI of (R)-(1-methylpyrrolidine-3-yl)methyl(3'-chloro-4'-fluoro-[1,1'-biphenyl]-2-yl)carbamate oxalate was prepared. Accordingly, the resulting XRPD pattern was shown in FIG. 17.

EXAMPLE 17

Figure 18:
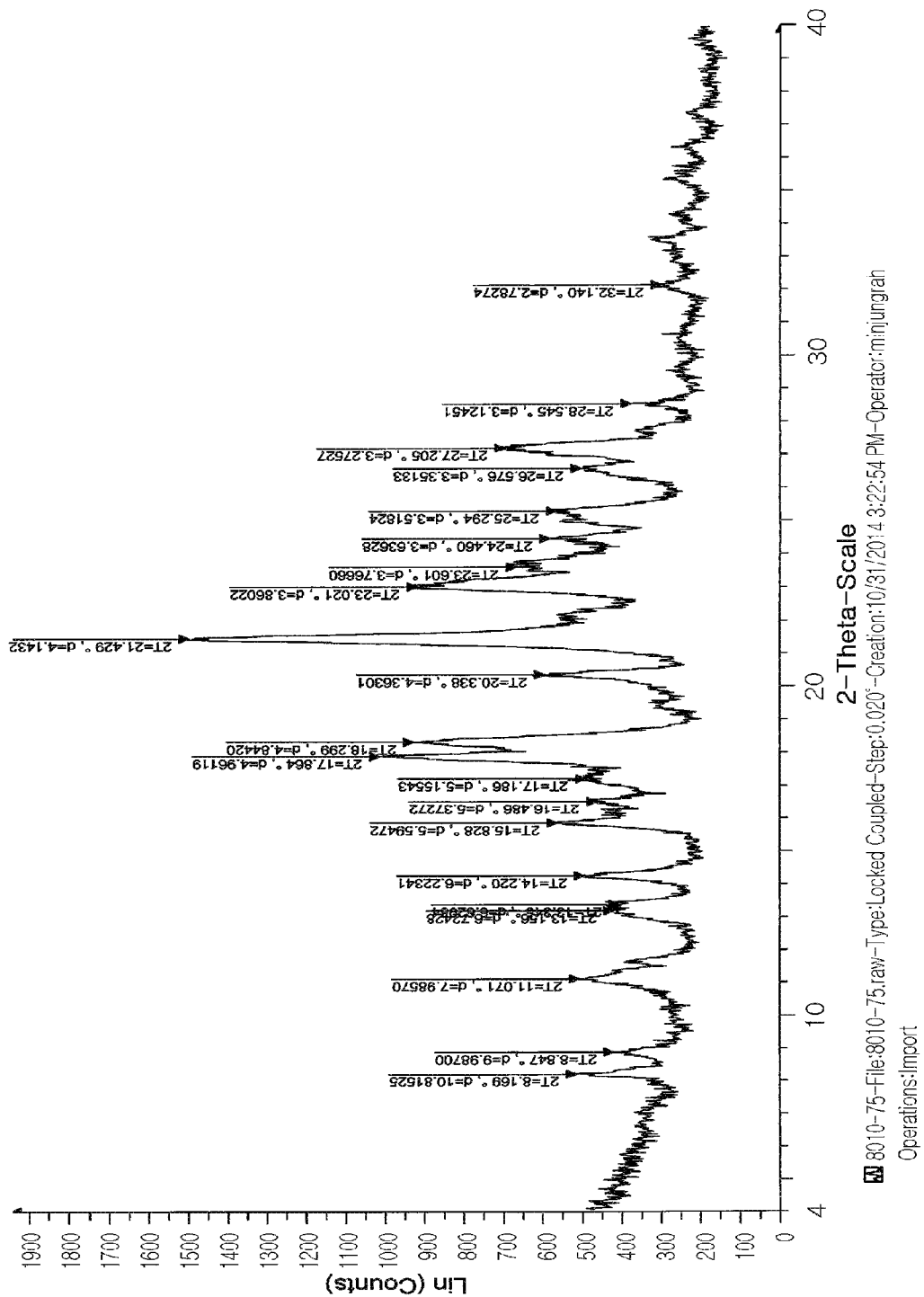
FIG. 18 is a graph of showing the XRPD results of a form VII of (R)-(1-methylpyrrolidine-3-yl)methyl(3'-chloro-4'-fluoro-[1,1'-biphenyl]-2-yl)carbamate oxalate.

Preparation of a Form VII of (R)-(1-methylpyrrolidine-3-yl)methyl(3'-chloro-4'-fluoro-[1,1'-biphenyl]-2-yl)carbamate oxalate The form II of (R)-(1-methylpyrrolidine-3-yl)methyl(3'-chloro-4'-fluoro-[1,1'-biphenyl]-2-yl)carbamate oxalate (0.5154 g) was dissolved in ethanol (20 mL), and then heated and dissolved up to 45° C. while being stirred. Benzene (38 mL) was added into a resulting mixture, after which benzene was added thereinto by 30 mL respectively three times. A resulting mixture was immediately filtered, after which an undissolved crystal was filtered out, and then a filtrate was kept at room temperature. After that, the resulting filtrate was moved into the silica gel desiccator at room temperature, then left alone for about two weeks, and then dried, such that a form VII of (R)-(1-methylpyrrolidine-3-yl)methyl(3'-chloro-4'-fluoro-[1,1'-biphenyl]-2-yl)carbamate oxalate was prepared. Accordingly, the resulting XRPD pattern was shown in FIG. 18.

EXAMPLE 18

Figure 19:
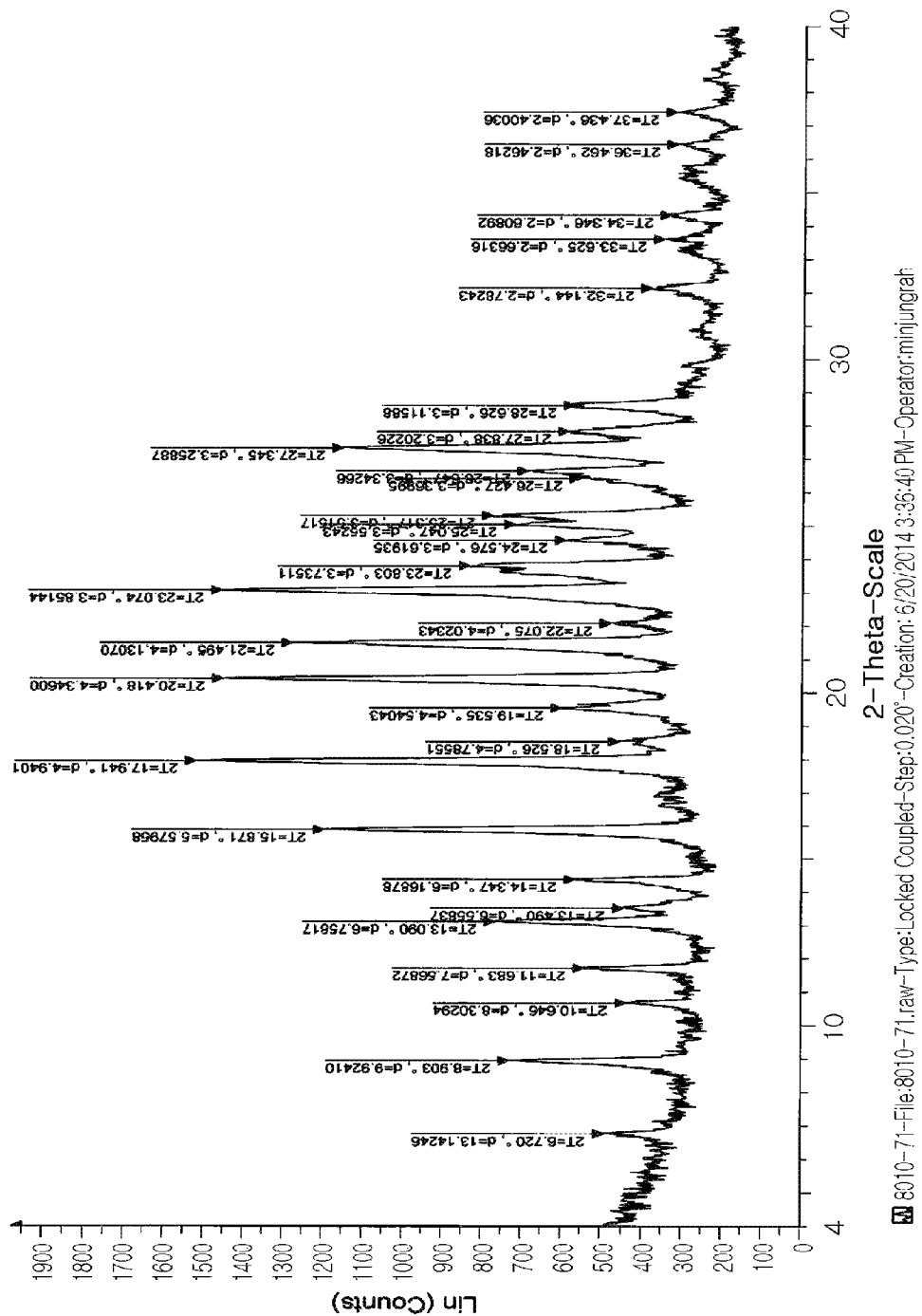
FIG. 19 is a graph of showing the XRPD results of a form VIII of (R)-(1-methylpyrrolidine-3-yl)methyl(3'-chloro-4'-fluoro-[1,1'-biphenyl]-2-yl)carbamate oxalate.

Preparation of a Form VIII of (R)-(1-methylpyrrolidine-3-yl)methyl(3'-chloro-4'-fluoro-[1,1'-biphenyl]-2-yl)carbamate oxalate The form II of (R)-(1-methylpyrrolidine-3-yl)methyl(3'-chloro-4'-fluoro-[1,1'-biphenyl]-2-yl)carbamate oxalate (0.5519 g) was dissolved in ethanol (20 mL), and then heated and dissolved up to 45° C. while being stirred. Benzene (128 mL) was added thereinto at once, and immediately filtered, after which an undissolved crystal was filtered out, and then a filtrate was kept at room temperature. After that, the resulting filtrate was moved into the silica gel desiccator at room temperature, then left alone for about two weeks, and then dried, such that a form VIII of (R)-(1-methylpyrrolidine-3-yl)methyl(3'-chloro-4'-fluoro-[1,1'-biphenyl]-2-yl)carbamate oxalate was prepared. Accordingly, the resulting XRPD pattern was shown in FIG. 19.

EXPERIMENTAL EXAMPLE 1

Stress Stability in a Solid State

A stress test (stress condition: 60° C. and a relative humidity of 90%) was performed on the (R)-(1-methylpyrrolidine-3-yl)methyl(3'-chloro-4'-fluoro-[1,1'-biphenyl]-2-yl)carbamate oxalate prepared in Example 1 above and the (R)-(1-methylpyrrolidine-3-yl)methyl(3'-chloro-4'-fluoro-[1,1'-biphenyl]-2-yl)carbamate citrate and the (R)-(1-methylpyrrolidine-3-yl)methyl(3'-chloro-4'-fluoro-[1,1'-biphenyl]-2-yl)carbamate phosphate prepared in Comparative Examples 1 and 2, wherein results of analyzing relative purities (%)/properties were shown in Table 1.

TABLE 1

|  | Oxalate | | | Citrate | | | Phosphate | | |
| --- | --- | --- | --- | --- | --- | --- | --- | --- | --- |
|  | initial | Week 1 | Week 2 | initial | Week 1 | Week 2 | initial | Week 1 | Week 2 |
| 60° C. | 99.3/ Solid | 99.3/ Solid | 99.4/ Solid | 97.7/ Solid | 97.8/ Dissolved | 97.9/ Dissolved | 98.4/ Solid | 98.4/ Dissolved | 98.4/ Dissolved |
| RH 90% |  | 99.3/ Solid | 99.4/ Solid |  | 97.7/ Dissolved | 97.7/ Dissolved |  | 98.4/ Dissolved | 98.4/ Dissolved |

As shown in Table 1 above, it may be identified that the (R)-(1-methylpyrrolidine-3-yl)methyl(3'-chloro-4'-fluoro-[1,1'-biphenyl]carbamate oxalate, the (R)-(1-methylpyrrolidine-3-yl)methyl(3'-chloro-4'-fluoro-[1,1'-biphenyl]-2-yl) carbamate citrate, and the (R)-(1-methylpyrrolidine-3-yl)methyl(3'-chloro-4'-fluoro-[1,1'-biphenyl]-2-yl)carbama phosphate do not show a change in purity under the stress condition, but the (R)(1-methylpyrrolidine-3-yl)methyl(3'-chloro-4'-fluoro-[1,1'-biphenyl]-2-yl)carbamate oxalate of the present invention is kept in an unmelted state, thus suggesting that such oxalate is suitable to be formulated into a preparation due to low hygroscopicity and excellent preservation stability.

EXPERIMENTAL EXAMPLE 2

Accelerated Stability in the Solid State

An accelerated test (accelerated condition: 40° C./RH 75%) was performed on the (R)-(1-methylpyrrolidine-3-yl)methyl(3'-chloro-4'-fluoro-[1,1'-biphenyl]-2-yl)carbamate oxalate prepared in Example 1 above and the (R)-(1-methylpyrrolidine-3-yl)methyl(3'-chloro-4'-fluoro-[1,1'-biphenyl]-2-yl)carbamate citrate and the (R)-(1-methylpyrrolidine-3-yl)methyl(3'-chloro-4'-fluoro-[1,1'-biphenyl]-2-yl)carbamate phosphate prepared in Comparative Examples 1 and 2, wherein analysis results thereof were shown in Table 2.

TABLE 2

| Test period | Salt | Relative purity (%) | Property |
| --- | --- | --- | --- |
| initial | Oxalate | 99.3 | Solid |
|  | Citrate | 97.7 | Solid |
|  | Phosphate | 98.4 | Solid |

TABLE 2-continued

| Test period | Salt | Relative purity (%) | Property |
|---|---|---|---|
| Week 1 | Oxalate | 99.3 | Solid |
|  | Citrate | 97.7 | Solid |
|  | Phosphate | 98.3 | Dissolved |
| Week 2 | Oxalate | 99.3 | Solid |
|  | Citrate | 97.6 | Solid |
|  | Phosphate | 98.3 | Dissolved |
| Week 3 | Oxalate | 99.3 | Solid |
|  | Citrate | 97.7 | Dissolved |
|  | Phosphate | 98.4 | Dissolved |
| Week 4 | Oxalate | 99.3 | Solid |
|  | Citrate | 97.4 | Dissolved |
|  | Phosphate | 98.4 | Dissolved |

As shown in Table 2 above, it may be seen that the (R)-(1-methylpyrrolidine-3-yl)methyl(3'-chloro-4'-fluoro-[1,1'-biphenyl]-2-yl)carbamate oxalate; (R)-(1-methylpyrrolidine-3-yl)methyl(3'-chloro-4'-fluoro-[1,1'-biphenyl]-2-yl) carbamate citrate; and (R)-(1-methylpyrrolidine-3-yl) methyl(3'-chloro-4'-fluoro-[1,1'-biphenyl]-2-yl)carbama phosphate do not show a change in purity under the accelerated condition just as in the stress test, but the citrate and phosphate show a melting phenomenon, thus suggesting that the citrate and phosphate are not physicochemically suitable salts.

Thus, it may be identified that the (R)-(1-methylpyrrolidine-3-yl)methyl(3'-chloro-4'-fluoro-[1,1'-biphenyl]-2-yl)carbamate oxalate of the present invention is stable in a preparation process, easy to handle, and useful for mass production.

EXPERIMENTAL EXAMPLE 3

Accelerated and Stress Stability of Forms I, II and III

The accelerated test (accelerated condition: 40° C./RH 75%) and the stress test (stress condition: 60° C.) were performed on the form I of (R)-(1-methylpyrrolidine-3-yl) methyl(3'-chloro-4'-fluoro-[1,1'-biphenyl]-2-yl)carbamate oxalate prepared in Example 2 above and the form II of (R)-(1-methylpyrrolidine-3-yl)methyl(3'-chloro-4'-fluoro-[1,1'-biphenyl]-2-yl)carbamate oxalate and the form III of (R)-(1-methylpyrrolidine-3-yl)methyl(3'-chloro-4'-fluoro-[1,1'-biphenyl]-2-yl)carbamate oxalate prepared in Examples 3 and 9, wherein analysis results thereof were shown in Table 3.

TABLE 3

|  | Crystal form | | | Relative purity (%) | | |
|---|---|---|---|---|---|---|
|  | form I | form II | form III | form I | form II | form III |
| Early | form I | form II | form III | 99.66 | 99.87 | 99.81 |
| 60° C. Week 1 | form I | form II | form III | 99.71 | 99.85 | 99.82 |
| 40° C./RH 75% Week 1 | form I | form II | form III | 99.55 | 99.83 | 99.79 |
| 60° C. Week 3 | form I | form II | form III | 99.61 | 99.79 | 99.79 |
| 40° C./RH 75% Week 3 | form I | form II | form III | 99.60 | 99.81 | 99.80 |

As shown in Table 3 above, it was shown that the forms I, II and III are all stable under the accelerated and stress conditions. Also, it may be seen that such crystal forms are not changed either, and the unique crystal forms are maintained.

While specific portions of the present invention have been described in detail above, it is apparent to those skilled in the art that such detailed descriptions are set forth to illustrate exemplary embodiments only, but are not construed to limit the scope of the present invention. Thus, it should be understood that the substantial scope of the present invention is defined by the accompanying claims and equivalents thereto.

The invention claimed is:

1. An (R)-(1-methylpyrrolidine-3-yl)methyl(3'-chloro-4'-fluoro-[1,1'-biphenyl]-2-yl)carbamate oxalate represented by a following formula 1:

[Formula 1]

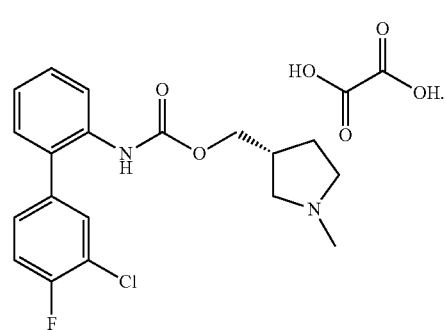

2. The (R)-(1-methylpyrrolidine-3-yl)methyl(3'-chloro-4'-fluoro-[1,1'-biphenyl]-2-yl)carbamate oxalate, according to claim 1, wherein the said (R)-(1-methylpyrrolidine-3-yl) methyl(3'-chloro-4'-fluoro-[1,1'-biphenyl]-2-yl)carbamate oxalate is a crystal.

3. A form I of (R)-(1-methylpyrrolidine-3-yl)methyl(3'-chloro-4'-fluoro-[1,1'-biphenyl]-2-yl)carbamate oxalate, wherein an X-ray powder diffraction (XRPD) pattern comprises at least three diffraction peaks selected from the group consisting of diffraction angles 2θ of 13.402±0.2°, 14.300±0.2°, 18.519±0.2°, 19.577±0.2° and 21.499±0.2°.

4. The form I of (R)-(1-methylpyrrolidine-3-yl)methyl(3'-chloro-4'-fluoro-[1,1'-biphenyl]-2-yl)carbamate oxalate, according to claim 3, wherein the XRPD pattern further comprises at least one diffraction peak selected from the group consisting of diffraction angles 2θ of 7.182±0.2°, 8.379±0.2°, 8.679±0.2°, 11.180±0.2°, 16.320±0.2°, 16.659±0.2°, 17.321±0.2°, 17.861±0.2°, 20.632±0.2°, 22.180±0.2°, 22.922±0.2°, 23.339±0.2°, 24.019±0.2°, 24.297±0.2°, 24.699±0.2°, 25.441±0.2°, 27.239±0.2° and 29.880±0.2°.

5. The form I of (R)-(1-methylpyrrolidine-3-yl)methyl(3'-chloro-4'-fluoro-[1,1'-biphenyl]-2-yl)carbamate oxalate, according to claim 3, wherein such form I has an onset temperature of 121.85° C. (±0.5° C.) and an endothermic peak of 126.96° C. (±0.5° C.) during a differential scanning calorimetry (DSC) analysis, if a heating rate is 20° C./min.

6. A method for preparing the form I of (R)-(1-methylpyrrolidine-3-yl)methyl(3'-chloro-4'-fluoro-[1,1'-biphenyl]-2-yl)carbamate oxalate of claim 3, wherein the method comprises steps of: dissolving a free base of (R)-(1-methylpyrrolidine-3-yl)methyl(3'-chloro-4'-fluoro-[1,1'-biphenyl]-2-yl)carbamate in acetone; inserting oxalic acid into the said solution and stirring the resulting mixture; and crystallizing the resulting mixture by means of methyl-t-butyl ether.

7. A form II of (R)-(1-methylpyrrolidine-3-yl)methyl(3'-chloro-4'-fluoro-[1,1'-biphenyl]-2-yl)carbamate oxalate, wherein the XRPD pattern comprises at least three diffraction peaks selected from the group consisting of diffraction angles 2θ of 13.439±0.2°, 14.481±0.2°, 18.501±0.2°, 21.779±0.2° and 23.358±0.2°.

8. The form II of (R)-(1-methylpyrrolidine-3-yl)methyl (3'-chloro-4'-fluoro-[1,1'-biphenyl]-2-yl)carbamate oxalate, according to claim 7, wherein the XRPD pattern further comprises at least one diffraction peak selected from the group consisting of diffraction angles 2θ of 8.360±0.2°, 11.340±0.2°, 16.401±0.2°, 16.739±0.2°, 17.360±0.2°, 17.938±0.2°, 22.179±0.2°, 24.299±0.2°, 24.641±0.2°, 25.500±0.2°, 26.422±0.2°, 27.260±0.2°, 28.201±0.2° and 29.878±0.2°.

9. The form II of (R)-(1-methylpyrrolidine-3-yl)methyl (3'-chloro-4'-fluoro-[1,1'-biphenyl]-2-yl)carbamate oxalate, according to claim 7, wherein such form II has the onset temperature of 127.39° C. (±0.5° C.) and the endothermic peak of 130.20° C. (±0.5° C.) during the DSC analysis, if the heating rate is 20° C./min.

10. A method for preparing the form II of (R)-(1-methylpyrrolidine-3-yl)methyl(3'-chloro-4'-fluoro-[1,1'-biphenyl]-2-yl)carbamate oxalate of claim 7, wherein the method includes a step of recrystallizing the form I of (R)-(1-methylpyrrolidine-3-yl)methyl(3'-chloro-4'-fluoro-[1,1'-biphenyl]-2-yl)carbamate oxalate by means of a recrystallization solvent selected from the group consisting of dichloromethane; acetone; heptane; methylethylketone; acetonitrile; and a mixture thereof.

11. A form III of (R)-(1-methylpyrrolidine-3-yl)methyl (3'-chloro-4'-fluoro-[1,1'-biphenyl]-2-yl)carbamate oxalate, wherein the XRPD pattern comprises at least three diffraction peaks selected from the group consisting of diffraction angles 2θ of 10.720±0.2°, 11.018±0.2°, 14.239±0.2°, 17.880±0.2° and 21.440±0.2°.

12. The form III of (R)-(1-methylpyrrolidine-3-yl)methyl (3'-chloro-4'-fluoro-[1,1'-biphenyl]-2-yl)carbamate oxalate, according to claim 11, wherein the XRPD pattern further comprises at least one diffraction peak selected from the group consisting of diffraction angles 2θ of 8.700±0.2°, 13.098±0.2°, 14.959±0.2°, 15.382±0.2°, 16.701±0.2°, 17.309±0.2°, 18.680±0.2°, 19.561±0.2°, 20.560±0.2°, 22.042±0.2°, 22.762±0.2°, 23.940±0.2°, 24.141±0.2°, 26.855±0.2°, 27.379±0.2° and 29.006±0.2°.

13. The form III of (R)-(1-methylpyrrolidine-3-yl)methyl (3'-chloro-4'-fluoro-[1,1'-biphenyl]-2-yl)carbamate oxalate, according to claim 11, wherein such form III has the onset temperature of 123.68° C. (±0.5° C.) and the endothermic peak of 128.37° C. (±0.5° C.) during the DSC analysis, if the heating rate is 20° C./min.

14. A method for preparing the form III of (R)-(1-methylpyrrolidine-3-yl)methyl(3'-chloro-4'-fluoro-[1,1'-biphenyl]-2-yl)carbamate oxalate of claim 11, wherein the method includes the step of recrystallizing the form I of (R)-(1-methylpyrrolidine-3-yl)methyl(3'-chloro-4'-fluoro-[1,1'-biphenyl]-2-yl)carbamate oxalate by means of the recrystallization solvent selected from the group consisting of ethanol; methyl-t-butyl ether; heptane; 1,4-dioxane; isopropyl acetate; dichloromethane; isopropanol; and a mixture thereof.

15. A form IV of (R)-(1-methylpyrrolidine-3-yl)methyl (3'-chloro-4'-fluoro-[1,1'-biphenyl]-2-yl)carbamate oxalate, wherein the XRPD pattern comprises at least three diffraction peaks selected from the group consisting of diffraction angles 2θ of 16.642±0.2°, 17.839±0.2°, 20.981±0.2°, 21.580±0.2° and 22.701±0.2°.

16. The form IV of (R)-(1-methylpyrrolidine-3-yl)methyl (3'-chloro-4'-fluoro-[1,1'-biphenyl]-2-yl)carbamate oxalate, according to claim 15, wherein the XRPD pattern further comprises at least one diffraction peak selected from the group consisting of diffraction angles 2θ of 8.355±0.2°, 11.415±0.2°, 13.419±0.2°, 13.956±0.2°, 15.619±0.2°, 18.579±0.2°, 23.219±0.2°, 24.720±0.2°, 26.478±0.2°, 27.195±0.2°, 28.143±0.2° and 29.172±0.2°.

17. The form IV of (R)-(1-methylpyrrolidine-3-yl)methyl (3'-chloro-4'-fluoro-[1,1'-biphenyl]-2-yl)carbamate oxalate, according to claim 15, wherein such form IV has the onset temperature of 120.60° C. (±0.5° C.) and the endothermic peak of 126.88° C. (±0.5° C.) during the DSC analysis, if the heating rate is 20° C./min.

18. A method for preparing the form IV of (R)-(1-methylpyrrolidine-3-yl)methyl(3'-chloro-4'-fluoro-[1,1'-biphenyl]-2-yl)carbamate oxalate of claim 15, wherein the method includes the step of recrystallizing the form I of (R)-(1-methylpyrrolidine-3-yl)methyl(3'-chloro-4'-fluoro-[1,1'-biphenyl]-2-yl)carbamate oxalate by means of 1,4-dioxane.

19. A form V of (R)-(1-methylpyrrolidine-3-yl)methyl(3'-chloro-4'-fluoro-[1,1'-biphenyl]-2-yl)carbamate oxalate, wherein the XRPD pattern comprises at least three diffraction peaks selected from the group consisting of diffraction angles 2θ of 10.925±0.2°, 14.200±0.2°, 20.559±0.2° and 21.396±0.2°.

20. The form V of (R)-(1-methylpyrrolidine-3-yl)methyl (3'-chloro-4'-fluoro-[1,1'-biphenyl]-2-yl)carbamate oxalate, according to claim 19, wherein the XRPD pattern further comprises at least one diffraction peak selected from the group consisting of diffraction angles 2θ of 7.049±0.2°, 8.592±0.2°, 16.081±0.2°, 17.226±0.2°, 17.840±0.2° and 19.565±0.2°.

21. A method for preparing the form V of (R)-(1-methylpyrrolidine-3-yl)methyl(3'-chloro-4'-fluoro-[1,1'-biphenyl]-2-yl)carbamate oxalate of claim 19, wherein the method comprises the step of recrystallizing the form II of (R)-(1-methylpyrrolidine-3-yl)methyl(3'-chloro-4'-fluoro-[1,1'-biphenyl]-2-yl)carbamate oxalate by means of butanol.

22. A form VI of (R)-(1-methylpyrrolidine-3-yl)methyl (3'-chloro-4'-fluoro-[1,1'-biphenyl]-2-yl)carbamate oxalate, wherein the XRPD pattern comprises at least three diffraction peaks selected from the group consisting of diffraction angles 2θ of 10.127±0.2°, 10.893±0.2°, 11.751±0.2° and 17.978±0.2°.

23. The form VI of (R)-(1-methylpyrrolidine-3-yl)methyl (3'-chloro-4'-fluoro-[1,1'-biphenyl]-2-yl)carbamate oxalate, according to claim 22, wherein the XRPD pattern further comprises at least one diffraction peak selected from the group consisting of diffraction angles 2θ of 7.150±0.2°, 14.362±0.2°, 14.654±0.2°, 15.251±0.2° and 16.360±0.2°.

24. A method for preparing the form VI of (R)-(1-methylpyrrolidine-3-yl)methyl(3'-chloro-4'-fluoro-[1,1'-biphenyl]-2-yl)carbamate oxalate of claim 22, wherein the method comprises the step of recrystallizing the form II of (R)-(1-methylpyrrolidine-3-yl)methyl(3'-chloro-4'-fluoro-[1,1'-biphenyl]-2-yl)carbamate oxalate by means of methanol.

25. A form VII of (R)-(1-methylpyrrolidine-3-yl)methyl (3'-chloro-4'-fluoro-[1,1'-biphenyl]-2-yl)carbamate oxalate, wherein the XRPD pattern comprises at least three diffraction peaks selected from the group consisting of diffraction angles 2θ of 8.169±0.2°, 8.847±0.2°, 11.071±0.2° and 13.156±0.2°.

26. The form VII of (R)-(1-methylpyrrolidine-3-yl)methyl(3'-chloro-4'-fluoro-[1,1'-biphenyl]-2-yl)carbamate oxalate, according to claim 25, wherein the XRPD pattern further comprises at least one diffraction peak selected from the group consisting of diffraction angles 2θ of 13.345±0.2°, 14.220±0.2°, 15.828±0.2°, 16.486±0.2° and 17.186±0.2°.

27. A method for preparing the form VII of (R)-(1-methylpyrrolidine-3-yl)methyl(3'-chloro-4'-fluoro-[1,1'-biphenyl]-2-yl)carbamate oxalate of claim 25, wherein the method comprises the step of recrystallizing the form II of (R)-(1-methylpyrrolidine-3-yl)methyl(3'-chloro-4'-fluoro-[1,1'-biphenyl]-2-yl)carbamate oxalate by means of the recrystallization solvent selected from the group consisting of ethanol; benzene; and a mixture thereof.

28. A form VIII of (R)-(1-methylpyrrolidine-3-yl)methyl(3'-chloro-4'-fluoro-[1,1'-biphenyl]-2-yl)carbamate oxalate, wherein the XRPD pattern comprises at least three diffraction peaks selected from the group consisting of diffraction angles 2θ of 8.903±0.2°, 13.090±0.2°, 14.347±0.2° and 15.871±0.2°.

29. The form VIII of (R)-(1-methylpyrrolidine-3-yl)methyl(3'-chloro-4'-fluoro-[1,1'-biphenyl]-2-yl)carbamate oxalate, according to claim 28, wherein the XRPD pattern further comprises at least one diffraction peak selected from the group consisting of diffraction angles 2θ of 6.720±0.2°, 10.646±0.2°, 11.683±0.2°, 13.490±0.2° and 17.941±0.2°.

30. A method for preparing the form VIII of (R)-(1-methylpyrrolidine-3-yl)methyl(3'-chloro-4'-fluoro-[1,1'-biphenyl]-2-yl)carbamate oxalate of claim 28, wherein the method comprises the step of recrystallizing the form II of (R)-(1-methylpyrrolidine-3-yl)methyl(3'-chloro-4'-fluoro-[1,1'-biphenyl]-2-yl)carbamate oxalate by means of the recrystallization solvent selected from the group consisting of ethanol; benzene; and a mixture thereof.

31. A method for treating a disease selected from the group of consisting of a chronic obstructive pulmonary disease, asthma, irritable bowel syndrome, urinary incontinence, rhinitis, spasmodic colitis, chronic cystitis, Alzheimer's disease, senile dementia, glaucoma, schizophrenia, gastroesophageal reflux disease, cardiac arrhythmia, hypersalivation syndrome, enuresis, nervous pollakiuria, neurogenic bladder, unstable bladder, cystospasm and pollakisuria, comprising:
administering an effective amount of a muscarine M3 receptor antagonist to a subject in need thereof;
wherein the muscarine M3 receptor antagonist comprises (R)-(1-methylpyrrolidine-3-yl)methyl(3'-chloro-4'-fluoro-[1,1'-biphenyl]-2-yl)carbamate oxalate according to claim 1 as an effective component.

32. A pharmaceutical composition, comprising:
the (R)-(1-methylpyrrolidine-3-yl)methyl(3'-chloro-4'-fluoro-[1,1'-biphenyl]-2-yl)carbamate oxalate of claim 1; and
a pharmaceutically acceptable carrier.

* * * * *

UNITED STATES PATENT AND TRADEMARK OFFICE
CERTIFICATE OF CORRECTION

PATENT NO. : 10,894,768 B2
APPLICATION NO. : 16/328492
DATED : January 19, 2021
INVENTOR(S) : Woo Young Kwak et al.

It is certified that error appears in the above-identified patent and that said Letters Patent is hereby corrected as shown below:

On the Title Page

Item (54) and in the Specification, Column 1, Lines 1-5 In the Title: delete "SALT OF (R)-($_1$-METHYLPYRROLIDINE-$_3$-YL)METHYL($_3$'-CHLORO-$_4$'-FLUORO-[$_{1,1}$'-BIPHENYL]-$_2$-YL)CARBAMATE AND CRYSTAL FORM THEREOF" and insert -- SALT OF (R)-(1-METHYLPYRROLIDINE-3-YL)METHYL(3'-CHLORO-4'-FLUORO-[1,1'-BIPHENYL]-2-YL)CARBAMATE AND CRYSTAL FORM THEREOF --, therefor.

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*